(12) United States Patent
Pagnon et al.

(10) Patent No.: US 10,065,427 B2
(45) Date of Patent: Sep. 4, 2018

(54) FLOW METER AND USE THEREOF IN A PRINTER

(71) Applicant: Dover Europe Sàrl, Vernier (CH)

(72) Inventors: Alain Pagnon, Bourg les Valence (FR); Joao Paulo Ribeiro, Guilherand Granges (FR)

(73) Assignee: DOVER EUROPE SÀRL, Vernier Suisse (CH)

( * ) Notice: Subject to any disclaimer, the term of this patent is extended or adjusted under 35 U.S.C. 154(b) by 0 days.

(21) Appl. No.: 15/465,888

(22) Filed: Mar. 22, 2017

(65) Prior Publication Data
US 2017/0274667 A1    Sep. 28, 2017

(30) Foreign Application Priority Data

Mar. 22, 2016  (FR) ..................... 16 52439

(51) Int. Cl.
| | | |
|---|---|---|
| *B41J 2/175* | (2006.01) | |
| *B41J 2/03* | (2006.01) | |
| *G01D 1/00* | (2006.01) | |
| *G01N 11/08* | (2006.01) | |

(52) U.S. Cl.
CPC ............ *B41J 2/17566* (2013.01); *B41J 2/03* (2013.01); *B41J 2/175* (2013.01); *G01D 1/00* (2013.01); *G01N 11/08* (2013.01)

(58) Field of Classification Search
CPC .......... B01J 2219/00378; B01L 3/0268; B01L 3/0265; B01L 2400/0487; G01N 2035/1041; G01N 9/32; G01N 11/08
See application file for complete search history.

(56) References Cited

U.S. PATENT DOCUMENTS

| | | | | |
|---|---|---|---|---|
| 4,600,928 A | * | 7/1986 | Braun ................. | B41J 2/16552 347/27 |
| 4,641,535 A | | 2/1987 | Malguarnera | |
| 4,905,503 A | * | 3/1990 | Langrick ................. | B41J 2/195 73/54.06 |
| 5,927,547 A | * | 7/1999 | Papen .................. | B01L 3/0268 222/333 |

(Continued)

FOREIGN PATENT DOCUMENTS

| | | |
|---|---|---|
| DE | 10 2005 024 575 A1 | 12/2006 |
| EP | 0 123 523 A2 | 10/1984 |

(Continued)

OTHER PUBLICATIONS

M.A. Boillat et al., "A Differential Pressure Liquid Flow Sensor for Flow Regulation and Dosing Systems" IEEE, 1995.

(Continued)

*Primary Examiner* — John P Zimmermann
(74) *Attorney, Agent, or Firm* — Pearne & Gordon LLP

(57) ABSTRACT

A device (20) for measuring the flow rate of ink sent to a print head of an ink jet printer, comprising: a restriction (22) of the diameter of the flow of ink, arranged in the path thereof, sensors (26, 28) for measuring the pressure difference ($P_{in}-P_{out}$), between the pressure of fluid upstream of the restriction ($P_{in}$) and the pressure of ink downstream of the restriction ($P_{out}$).

21 Claims, 9 Drawing Sheets

(56) References Cited

U.S. PATENT DOCUMENTS

| | | | |
|---|---|---|---|
| 6,537,817 B1 * | 3/2003 | Papen | B01L 3/0268 134/22.11 |
| 7,192,121 B2 | 3/2007 | Barbet | |
| 8,540,350 B2 | 9/2013 | Barbet | |
| 9,844,936 B2 * | 12/2017 | Barbet | B41J 2/14008 |
| 2009/0032064 A1 * | 2/2009 | Gifford | B08B 3/044 134/18 |
| 2016/0347074 A1 | 12/2016 | Ribeiro | |

FOREIGN PATENT DOCUMENTS

| | | |
|---|---|---|
| EP | 0 287 372 A1 | 10/1988 |
| EP | 0 329 354 A2 | 8/1989 |
| EP | 2 075 552 A2 | 7/2009 |
| FR | 2 851 495 A1 | 8/2004 |
| FR | 2 952 851 A1 | 5/2011 |
| GB | 1 408 657 | 10/1975 |
| JP | S54-021723 A | 2/1979 |
| JP | H09-201980 A | 8/1997 |
| WO | 01/28701 A1 | 4/2001 |

OTHER PUBLICATIONS

French Search Report issued in French Patent Application No. FR 1652440 dated Nov. 30, 2016.
French Search Report issued in French Patent Application No. FR 1652439 dated Dec. 16, 2016.
Extended European Search Report issued in Patent Application No. EP 17 16 2430 dated Jun. 16, 2017.
French Search Report issued in French Patent Application No. FR 1657863 dated Dec. 16, 2016.
Extended European Search Report issued in Patent Application No. 17 16 2436 dated Jun. 26, 2017.
Extended European Search Report issued in Patent Application No. 17 162 439.8 dated Jun. 19, 2017.
European Office action for EP 17 162 439.8 dated May 25, 2018.
Helmut Kipphan: "Handbook of Print Media", 2000, pp. 65-66, Springer Verlag, Berlin Heidelberg New York.

* cited by examiner

FLOW METER AND USE THEREOF IN A PRINTER

TECHNICAL FIELD AND PRIOR ART

The invention relates to continuous ink jet printers, in particular but not exclusively binary continuous ink jet printers provided with a multi-nozzle drop generator. It targets in particular an improvement to a circuit for supplying and recovering ink and solvent of these printers.

Continuous ink jet printers include:
an ink drop generator,
means for separating the trajectories of the drops produced by the generator and directing them to a printing support or to a recovery gutter.

In FIG. 1 is represented the main units of an ink jet printer. The printer comprises a console 300, a compartment 400 containing notably circuits for conditioning ink and solvents, as well as reservoirs for ink and solvents. Generally the compartment 400 is in the lower part of the console. The upper part of the console comprises the command and control electronics as well as visualisation means. The console is hydraulically and electrically connected to a print head 100 via an umbilical 200. A gantry, not represented, makes it possible to install the print head facing a printing support 800.

The printing support 800 moves along a direction materialised by an arrow. This direction is perpendicular to an alignment axis of the nozzles.

The drop generator includes nozzles aligned on a nozzle plate along an X axis of alignment of the nozzles. During printing, jets of ink are ejected in a continuous manner by these nozzles in a direction Z perpendicular to the nozzle plate. Among continuous ink jet printers may be distinguished deviated continuous ink jet printers and binary continuous ink jet printers. In multi-deflection deviated continuous ink jet printers, the drops formed from a nozzle during printing of a position of a printing support are deflected or non-deflected. For each printing position and for each nozzle, a segment perpendicular to the direction of movement of the printing support is printed. The deflected drops are deflected in such a way that they are going to strike the printing support on the part of the printed segment that has to be printed taking account of the pattern to print. Non-deflected drops are recovered by a recovery gutter. Deviated continuous ink jet printers in general comprise few injection nozzles, but each nozzle can print, for each printing position of the support, several pixels spread out on the printing segment as a function of the pattern to print.

In binary continuous ink jet printers, ink coming from a nozzle only prints one pixel per printing position. The pixel considered does not receive any drop or receives one or more drops, as a function of the pattern to print. Hence, for good printing rapidity, the nozzle plate comprises a large number of nozzles, for example 64, enabling the simultaneous printing of as many pixels as nozzles. Drops not intended for printing are recovered by a recovery gutter. Such printers and print heads with continuous jets have been widely documented.

A general structure of print head for a binary continuous ink jet printer is explained below, in relation with FIG. 2.

The head represented includes a drop generator 11. On a nozzle plate 2 are aligned, along an X axis, a whole number n of nozzles 4, of which a first $4_1$ and a last nozzle $4_n$.

The first and last nozzles ($4_1$, $4n$) are the nozzles the furthest away from each other.

Each nozzle has an axis of emission of a jet parallel to a direction or a Z axis (situated in the plane of FIG. 2), perpendicular to the nozzle plate and to the X axis mentioned previously. A third axis, Y, is perpendicular to each of the two axes X and Z, the two axes X and Z extending in the plane of FIG. 2.

Each nozzle is in hydraulic communication with a pressurised stimulation chamber. The drop generator comprises as many stimulation chambers as nozzles. Each chamber is equipped with an actuator, for example a piezoelectric crystal, the command of which makes it possible to cut the continuous jet of ink into drops or sections. An example of design of a stimulation chamber is described in the document U.S. Pat. No. 7,192,121.

Downstream of the nozzle plate are located means, or sorting unit, 6 which make it possible to separate drops intended for printing from drops or sections of jets that do not serve for printing. In FIG. 2 is represented a trajectory a of drops of ink passing through a slot 17 (represented in broken lines in FIG. 2), and a trajectory b of drops of ink directed to a recovery gutter 7. The slot is open on the outside of the cavity and enables drops of ink intended for printing to get out; it is parallel to the direction X of alignment of the nozzles, the axes of direction Z of the nozzles passing through this slot, which is located on the face opposite to the nozzle plate 2. The slot and the gutter have, in the direction X, a length at least equal to the distance between the first and last nozzle.

The drops emitted or sections of jets, emitted by a nozzle and intended for printing, follow a trajectory a along the Z axis of the nozzle, then are going to strike a printing support 800, after having passed via the outlet slot 17.

The drops emitted, or sections of jets emitted, by a nozzle and not intended for printing are deviated by the means 6 (they follow a trajectory such as the trajectory b) and are recovered by the recovery gutter 7 then recycled.

Reference could be made, notably with regard to the formation of the jets and their break up to form drops, as well as with regard to the deflection of the drops, for example to the document U.S. Pat. No. 8,540,350 (FR 2 952 851) which describes a method for avoiding crosstalk between jets coming from nozzles adjacent to each other.

Reference could also be made to the prior art described in the U.S. Pat. No. 7,192,121 (FR 2851495) relative to the jet break up positions depending on whether a drop formed by the break up of the jet is intended or not to strike the printing support.

For single jet printers, knowledge of the jet speed (obtained with a dedicated means) suffices to assure the control of the pressure. In fact, the pressure of the circuit is servo-controlled so as to obtain and maintain the target jet speed.

For a twin jet CIJ printer, knowledge of the speed of the two jets is generally used to ensure the control of the pressure of the circuit. The average of the speeds of the two jets is often chosen as the target speed to reach.

For a printer with n-jets (n of the order of 32, 64, 128 or more) the principle of controlling with the average of the jet speeds is only applicable if dedicated costly and complex means are implemented to measure the individual speed of the jets.

The problem is thus posed, in particular in a printer with n-jets (n≥2), of finding a simple to implement device, which makes it possible to obtain the speed of the different jets.

Furthermore, another problem is that of the measurement of the viscosity of an ink used during printing operations using an ink jet printer, in particular of multi-jet type.

Viscosity is a parameter of the ink, of which potential variations may affect printing quality.

The problem is thus posed, notably in a printer with n-jets (n≥2), of finding a device that is simple to implement, which make it possible to obtain the viscosity of the ink.

Preferably such a device and/or method are adaptable to a CIJ type printer, with a single jet.

BRIEF DESCRIPTION OF THE INVENTION

The present invention firstly relates to a device for measuring flow rate, for an ink that may be sent to a print head, for example multi-jet or with a single jet, of an ink jet printer, comprising:
- a restriction of the diameter of the flow of ink, arranged in the path thereof,
- means for measuring the pressure difference ($P_{in}-P_{out}$), between the pressure of fluid upstream of the restriction ($P_{in}$) and the pressure of ink downstream of the restriction ($P_{out}$).

A device, or flow meter, according to the invention makes it possible to measure in an overall manner the flow rate of the set of jets of a multi-jet print head, and is particularly suited when the individual speed of each jet is not known. It makes it possible in fact to then obtain a measurement of the average speed of the jets.

Indeed, the nozzles of the printers preferably have identical, or similar, geometric characteristics.

This geometric similarity of the nozzles makes it possible to merge speed and flow rate for several nozzles delivering in parallel (as is the case in a multi-jet printer). The error associated with the fact of merging the averages of the speeds of the jets and total flow rate of all the jets is very small and in keeping with the expected quality of the control (or servo-control) (with a precision of 2% for example).

A device, or flow meter, according to the invention is moreover suited to a CIJ type head, with a single jet.

A device according to the invention may further comprise means for calculating the flow rate of ink as a function of the pressure difference ($P_{in}-P_{out}$).

Said means may be capable of calculating the flow rate as a function of the hydraulic characteristics ($\alpha$, $\beta$) of the restriction ($\alpha$ being the singular head loss coefficient and $\beta$ the regular head loss coefficient), the specific gravity or volumetric mass density ($\rho$) (also called density, in kg/m$^3$ for example) and the viscosity ($\mu$) of the ink, and the pressure difference ($P_{in}-P_{out}$).

Such a device may further comprise means for measuring the viscosity of ink.

The means for measuring pressure difference may comprise:
- a device for measuring the differential pressure between the pressure of fluid upstream of the restriction and the pressure of fluid downstream of the restriction;
- or a device for measuring pressure and means for placing the latter in fluidic communication alternatively with fluid upstream of the orifice and fluid downstream of the orifice;
- or a 1$^{st}$ device for measuring the pressure of ink upstream of the orifice and a 2$^{nd}$ device for measuring the pressure of ink downstream of the orifice.

In this case, the following may be provided:
- means for opening or closing a fluidic communication between the 1$^{st}$ device for measuring pressure and the 2$^{nd}$ device for measuring pressure, and means for opening or closing a fluidic communication between the 2$^{nd}$ device for measuring pressure and a point of a conduit downstream of the orifice;
- and/or means for correcting, preferably as a function of temperature, a measurement difference, for at least one same pressure, between the 1$^{st}$ device for measuring pressure and the 2$^{nd}$ device for measuring pressure and/or a sensitivity error of at least one of the devices for measuring pressure.

At least one, or each, means for measuring pressure may comprise a flush membrane pressure sensor.

An other device for measuring the flow rate and the viscosity of ink of an ink jet printer may comprise a device for measuring the flow rate of ink, for example as above, and means for measuring viscosity. According to particular embodiments of this other device:
- the print head, for example multi-jet, comprises a pressure sensor, of which the measurement (of the pressure in the print head) that it supplies is going to make it possible to calculate or estimate the viscosity;
- and/or means may be provided for calculating the viscosity of ink as a function of the pressure (PHead) measured by the pressure sensor, for example as a function of the hydraulic characteristics ($\alpha$Head, $\beta$Head) of the print head, and the pressure measured by the pressure sensor;
- and/or means may be provided for correcting, preferably as a function of temperature, a measurement difference, for at least one pressure, between a pressure value of the head measured by the pressure sensor and said actual pressure;
- and/or the means for measuring viscosity may comprise a conduit, arranged in line or in series with the device for measuring ink flow rate (downstream or upstream therefrom), and means for measuring a pressure difference (Poutv−Pinv) between an inlet and an outlet of said conduit. According to a particular embodiment, a same common sensor makes it possible to measure:
- the pressure of ink downstream of the restriction and the pressure at the inlet of the conduit of the means for measuring viscosity,
- or the pressure of ink upstream of the restriction and the pressure at the outlet of the conduit of the means for measuring viscosity.

The present invention also relates to a circuit for supplying with ink and/or with solvent an ink jet printer, for example multi-jet, comprising a device for measuring the flow rate and potentially the viscosity of ink of an ink jet printer comprising a device such as one of those above, and means for controlling or servo-controlling or correcting the pressure and/or the viscosity of the ink supplied as a function of the measurements of the flow rate and the viscosity of the ink.

The present invention also relates to a fluidic connecting cable for multi-jet ink jet printer comprising a device for measuring flow rate, or flow rate and viscosity, such as one of those above.

The present invention also relates to an ink jet printer comprising:
- a print head, for example multi-jet;
- means for forming a flow of ink to send to said print head;
- a fluidic connecting cable between these means for forming a flow of ink and the print head;
- a device for measuring the flow rate of fluid, in particular ink, as one of those described above.

The multi-jet print head may comprise a pressure sensor.

The printer may further comprise means for calculating the viscosity of ink as a function of the pressure (PHead)

measured by the pressure sensor, for example as a function of the hydraulic characteristics (αHead, βHead) of the print head, and the pressure measured by the pressure sensor.

The printer may comprise means for correcting, preferably as a function of temperature, a measurement difference, for at least one pressure, between a pressure value of the head measured by the pressure sensor and said actual pressure.

The printer may comprise means for controlling or servo-controlling or correcting the pressure and/or the viscosity of ink as a function of the measurements of the flow rate and the viscosity of the ink.

The present invention also relates to an ink jet printer comprising:
- a device for measuring flow rate and/or viscosity, such as described above;
- means for forming a flow of fluid to send to the print head;
- a fluidic connecting cable between these means for forming a flow of fluid and the print head.

The present invention also relates to a method of printing using an ink jet printer, comprising a measurement of the flow rate and/or the viscosity of ink using a device for measuring flow rate and/or viscosity, such as one of those described above.

The present invention also relates to a method of printing using an ink jet printer, as mentioned above, further comprising a step of measuring the flow rate and/or the viscosity of ink and a step of correcting the flow rate and/or the viscosity of ink.

The present invention also relates to a method for measuring, for example using a device as mentioned above, the flow rate of ink sent to a multi-jet print head of an ink jet printer, in which:
- the ink is made to circulate in a restriction of the diameter of the flow of ink, arranged in the path thereof,
- the pressure difference ($P_{in}-P_{out}$) is measured, between the pressure of fluid upstream of the orifice ($P_{in}$) and the pressure of ink downstream of the orifice ($P_{out}$).

The flow rate of ink may then be calculated as a function of the pressure difference ($P_{in}-P_{out}$), for example as a function, moreover, of the hydraulic characteristics ($\alpha$, $\beta$) of a restriction through which the ink circulates, the specific gravity ($\rho$) or volumetric mass density ($\rho$) (also called density, for example in kg/m$^3$) and the viscosity ($\mu$) of the ink.

It is moreover possible to measure the viscosity of the ink, for example by:
- a measurement of the differential pressure between the pressure of fluid upstream of a restriction of the diameter of the flow of ink, arranged in the path thereof, and the pressure of fluid downstream of the restriction;
- or a device for measuring pressure and means for placing the latter in fluidic communication alternatively with fluid upstream of the restriction and fluid downstream of the restriction;
- or a 1$^{st}$ device for measuring the pressure of ink upstream of the restriction and a 2$^{nd}$ device for measuring the pressure of ink downstream of the restriction.

In this case, it is possible:
- to open or close a fluidic communication between the 1$^{st}$ device for measuring pressure and the 2$^{nd}$ device for measuring pressure, and to open or close a fluidic communication between the 2$^{nd}$ device for measuring pressure and a point of a conduit downstream of the orifice;
- and/or to correct, preferably as a function of temperature, a measurement difference, at one same pressure at least, between the 1$^{st}$ device for measuring pressure and the 2$^{nd}$ device for measuring pressure and/or a sensitivity error of at least one of the devices for measuring pressure.

BRIEF DESCRIPTION OF THE DRAWINGS

Other advantages of the invention will become clear at the same time as details will be given in an exemplary embodiment of the invention which will now be described with reference to the appended drawings in which.

DETAILED DESCRIPTION OF EMBODIMENTS

Figure 3A:
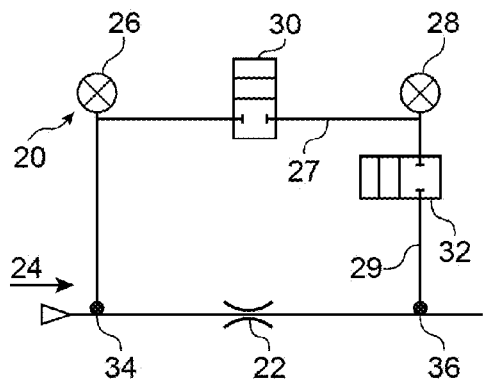
FIG. 3A is an exemplary embodiment of a flow meter according to the invention, applied to a circuit for supplying a print head of an ink jet printer with ink.

A first example of a flow meter 20 according to the invention is represented in FIG. 3A.

It comprises a calibrated orifice (or restriction) 22, arranged in the path of the fluid 24 of which the flow rate is to be measured. This restriction restricts the diameter through which the fluid flows; it imposes a pressure $P_{in}$, at its inlet, greater than that ($P_{out}$) at its outlet.

The orifice 22 is an orifice of inner passage diameter of the order of 0.5 mm, more generally comprised between 300 μm and 1 mm. The passage diameter of the fluid is preferably chosen so that the flow remains in the laminar domain with, for example, a Reynolds number less than 1000 (the laminar flow limit is 2300). The range from 300 µm to 1 mm enables this condition to be met for the flow rates of the printers concerned.

The orifice extends for example over a length l of several hundreds of micrometers, for example 400 µm, further for example comprised between 100 µm and 800 µm. It is sought to minimise this length, which plays directly on the regular head loss; but it is difficult to make, at an acceptable cost, an orifice over a small length; the resistance to head loss is also a criterion, a length of around 400 µm being an example making it possible to respond to the flow rates of the printers concerned.

This orifice forms a calibrated leakage or restriction. The diameters of the upstream and downstream conduits have for dimension that of the pipes of the circuit, 2.7 mm for example; these upstream and downstream diameters are large in view of the dimension of the orifice. This is going to represent a resistance in the path of the fluid, which leads to a local perturbation of the flow with, in particular, an accelerating effect (injector). This perturbation has a range limited to several mm and does not affect in any way flow at the level of the print head; one effect of the presence of this orifice is a head loss (very small in view of the operating pressure), which is going to lead to a slightly higher operating pressure. This pressure is imposed by a pump for pressurising ink, not represented in the figures.

A pressure sensor 26, preferably with flush membrane (which has a reduced dead volume), makes it possible to measure the inlet pressure (Pin) of the orifice, at a point 34 upstream of the orifice, preferably at several mm therefrom, for example at less than 1 cm.

A pressure sensor 28, once again preferably with flush membrane, makes it possible to measure the outlet pressure (Pout) of the orifice, at a point 36 downstream of the orifice, preferably at several mm therefrom, for example at less than 1 cm.

In a flush membrane pressure sensor, the pressure sensitive element is a flat membrane situated at one end of the sensor, which avoids any retention of fluid or material; thus, the membrane is flush with the measured flow. This avoids the presence of a cavity, above the diaphragm, which could collect fluid material from the measured flow which, in certain applications, may be very undesirable. The invention also makes it possible to use pressure sensors with non-flush membrane but the presence of a cavity, often synonymous with dead volume, degrades the operation of the assembly, notably on account of the steps of purging and cleaning implemented to use this type of sensor.

The sensors may be different to each other (while having the desired precision). But it is preferably that the 2 sensors are identical: it is in fact then easier to compensate errors of offset and linearity; if the sensors are different, compensation remains possible, but with an additional calculation taking into account the individual characteristics of each sensor.

In the embodiment illustrated, means or an element or organ 30 for placing in fluidic communication the 2 sensors, preferably a valve or an electromagnetic valve, with two orifices (inlet and outlet) and two positions (open or closed), makes it possible to connect or to place in fluidic communication the two pressure sensors 26 and 28, that is to say to enable these 2 elements to be placed at the same pressure.

Means or an element or an organ 32 for placing in fluidic communication the sensor 28 and the outlet of the flow meter, preferably a valve or an electromagnetic valve, with two orifices (inlet and outlet) and two positions (open or closed) makes it possible to connect or place in fluidic communication the pressure sensor 28 with the outlet of the flow meter, at the point 36. But a circulation of fluid by the elements 26, 30, 28, 32 is not necessary, except in the case of purging of the system.

When the valve 30 is closed and the valve 32 open, each of the sensors 26, 28 measures the pressure of the fluid, respectively upstream and downstream of the orifice 22. From these measurements, a pressure difference may be estimated or calculated and the flow rate may be estimated or calculated, as explained hereafter.

It is thus seen that, in the example illustrated, the means 26-32 are arranged along a conduit or a fluidic line 25, 27, 29, in parallel with the orifice 22, or with the flow of ink there through.

When the 2 valves 30 and 32 are open, the circulation of a cleaning liquid, for example solvent, makes it possible to clean the whole of the measurement line.

It is also possible to carry out an operation of purging the measurement line, to expel therefrom air that may be contained therein. The presence of air is in particular bothersome when it is wished to control the electromagnetic valves 30, 32 without influencing the flow rate traversing the orifice 22. Indeed, the presence of air in the measurement line transforms the behaviour of the fluid (which is an incompressible liquid) into a compressible fluid, so that, during transitory regimes, for example during the opening of an electromagnetic valve, fluid is consumed or supplied by the compression and decompression of air bubbles, which can perturb the pressure measurements which are assumed to be static. To carry out a purging of this air, the flow meter is supplied with a liquid (ink for example), the two electromagnetic valves 30, 32 being in the "open" state, which enables a flushing, with this liquid, of the line parallel to the orifice 22. The air contained in this line is thus driven along with the liquid and the system is thereby purged. Purging efficiency is improved if the sensor(s) has or have flush membrane(s). Preferably, the head losses through the restriction 22 are higher than in the parallel line in order to have a high flow rate, in the latter, at the moment of purging.

The implementation of two valves 30, 32, arranged as explained above, also makes it possible to carry out treatments with a view to the compensation of "offsets" (that is to say measurement differences between the two sensors 26 and 32 when they measure the same pressure) and/or errors or sensitivity differences between these sensors. This is easier to carry out if the sensors are identical than if they are different; in fact, the pressure differential that it is possible to calculate when the sensors are identical (they have in fact the same sensitivity) is considered; if the sensors are different, they do not have the same sensitivity, the calculation is then less direct but feasible.

When the electromagnetic valve 32 is closed and the electromagnetic valve 30 open, the two sensors 26, 28 are subjected to the same pressure, without flow. In so far as they can have different physical or technical characteristics (which are not strictly equal even if they are identical sensors or have an identical commercial reference) the values measured by these sensors (and their measuring chain) may also be different, so that the measured pressure difference value (Pin−Pout) is not zero. This difference is called the "offset" of the measurement system (difference in measurement value when the two sensors 26, 28 are subjected to the same pressure).

Measurement of the offset may be carried out several times, for example regularly, in order to compensate a possible drift over time. In particular a drift may arise on account of variations in temperature which can affect the 2 sensors 26, 28 in a different manner.

Advantageously, by carrying out this measurement while the pressure Pin is equal to the operating pressure (supplied by the ink circuit to obtain a appropriate jet speed), it is possible to compensate not only the "offset" errors of the sensors (values announced by the manufacturer of the sensor for a pressure relative to zero atmospheric pressure) but, also, the sensitivity errors of the sensors, which express the fact that the offset of the sensor changes as a function of the measured pressure value. Such errors may lead to measurement errors that are not in keeping with the required precision. An error correction due to the generalised "offset" (because it involves the offset at one operating pressure at least), contributes to obtaining better precision (better than 1%).

Figure 4A:
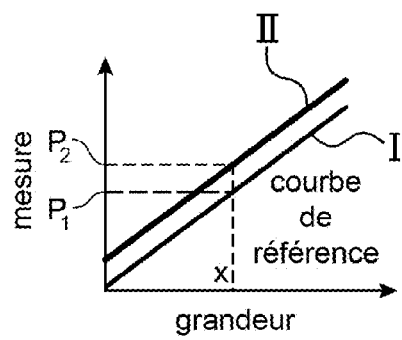
FIGS. 4A-4C are curves that illustrate the problem of measuring the "offset" and the linearity error between two sensors.

FIG. 4A illustrates the problem of the "offset" of a sensor. Curve I corresponds to the response of a perfect sensor (without offset), which corresponds to the measurement obtained as a function of the measured quantity. Curve II corresponds to the response of a sensor affected by an offset error. The curves are parallel but shifted. The difference between the two curves I and II defines the offset, or the measurement difference when the quantity measured is zero. This offset affects any measurement, that is to say that for any value X of the measured quantity, a constant difference is observed between the measurement and the real pressure value. The sensors 26 and 28 have different offset errors, when the difference ($P_{in}-P_{out}$) is calculated, the offset errors are accumulated but remain constant.

Figure 4B:
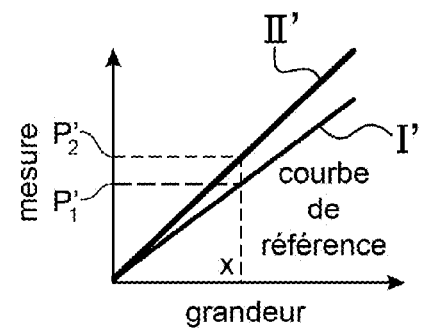

FIG. 4B illustrates the problem of the sensitivity of a sensor. Curve I corresponds to the response of a perfect sensor (without sensitivity drift), which corresponds to the measurement obtained as a function of the measured quantity. Curve II corresponds to the response of a sensor affected by a sensitivity error. These two curves, although having a common origin, have evolution differences; in FIG. 4B, these curves are straight lines, which do not have the same slopes and which thus form an angle between them. The difference between the two curves I' and II' defines a difference in sensitivity: for any value X of the measured quantity, a difference is observed between the measurement and the real pressure value. The sensors 26 and 28 have different sensitivity errors (the slopes of curve II are different), when the difference ($P_{in}-P_{out}$) is calculated, the sensitivity errors are accumulated. In fact the error generated is all the greater the bigger the value X to measure; this is known as sensitivity error (the error generated is, in the case illustrated in FIG. 4B, linear as a function of the quantity X to measure).

Figure 4C:
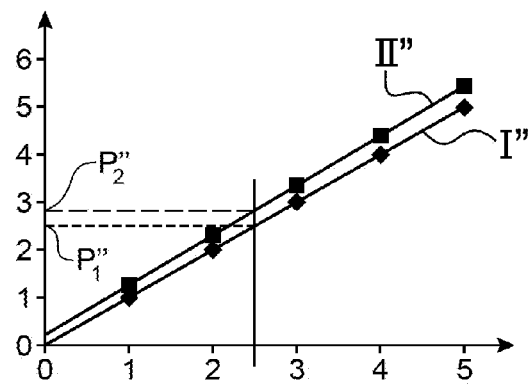

FIG. 4C illustrates the problem that results from the accumulation of offset problems and differences in sensitivities. In this example:

curve I″ corresponds to the case of a perfect sensor (no offset and no linearity error). The equation for this curve is: Measurement=X (quantity measured);

curve II″ integrates the offset and sensitivity errors. The equation for this curve is: Measurement=0.20+1.05*X.

It may be assumed that these curves correspond to those of the two sensors 26, 28.

For example, the sensor 26 has a response curve of equation:

$P_{in}=0.012+1.0025 \times P.$

And the sensor 28 has a response curve of equation:

$P_{out}=-0.008+0.9975 \times P.$

I.e. a real inlet pressure $P_{in}$ of 3.100 bars and a real outlet pressure $P_{out}$ of 3.000 bars.

The difference between the real pressures $P_{in}$ and $P_{out}$ is 0.100 bars (100 mbars).

Without compensation of any offset, the measurement of this pressure difference is:

$$\Delta P = (0.012 + 1.0025 \times 3.100) - (-0.008 + 0.9975 \times 3.000)$$
$$= (3.11975) - (2.9845)$$
$$= 0.13525 \text{ bars } (135 \text{ Mbars})$$

There is thus an error of 35%.

Within the scope of this example, it is possible to calculate the pressure difference when the compensation of the offset is taken into account.

The offset at zero relative pressure is: 0.012−(−0.008)= 0.020 bars (20 mbars)

Thus, the corrected ΔP of this offset is equal to:

$$\Delta P = ((0.012 + 1.0025 \times 3.100) - (-0.008 + 0.9975 \times 3.000)) -$$
$$((0.012) - (-(0.008)))$$
$$= ((3.11975) - (2.9845)) - (0.020))$$
$$= 0.11525 \text{ bars } (115 \text{ mbars}).$$

There is thus an error of 15%.

Within the scope of this same example, it is possible to calculate the pressure difference when account is taken of the compensation of the generalised offset, which takes account of the offset at zero relative pressure and the difference in sensitivity at the working pressure (offset of the two sensors at P=3.100 bars).

The generalised offset at 3.100 bars is then equal to:

(0.012+1.0025×3.100)−(−0.008+0.9975×3.100)

I.e.: (3.11975)−(3.08425)=0.0355 bars (35.5 mbars)

The corrected ΔP then becomes:

$$\Delta P = (( = 0.012 + 1.0025 \times 3.100) - (-0.008 + 0.9975 \times 3.000)) - (0.0355)$$
$$= ((3.11975) - (2.9845)) - (0.0355))$$
$$= 0.09975 \text{ bars } (99.75 \text{ mbars})$$

There is thus an error of 0.25%.

These examples show the interest of using the generalised offset and the steps and means for compensating it: the precision on the final measurement is considerably improved. Practically, it is possible to use the device described hereafter in relation with FIGS. 13A, 13B for measuring all these offset parameters. The results may be memorised and used for correcting measurements carried out later.

How the flow rate may be measured using the system described above in relation with FIG. 3A will now be described in greater detail.

This measurement of the flow rate may notably result from knowledge of the following parameters:

the hydraulic characteristics of the orifice 22, more exactly the two coefficients α and β, respectively characteristic of the singular and regular head losses of the orifice;

the physical characteristics of the fluid, in fact its specific gravity and its viscosity;

the pressure difference between the inlet pressure ($P_{in}$) and the outlet pressure ($P_{out}$) when the valve 30 is closed and the valve 32 open.

Potentially, if the offset, preferably generalised, is taken into account the pressure difference between the inlet pressure ($P_{in}$) and the outlet pressure ($P_{out}$) when the valve 30 is open and the valve 32 closed may be taken into account. The offset, preferably generalised, useful for obtaining the desired precision is then measured and the result obtained for the measurement is corrected.

By applying the Bernoulli relationship:

$$\tfrac{1}{2}\cdot\rho\cdot v^2+\rho\cdot g\cdot z+p=\text{constante}$$

where:
p is the pressure at one point (in Pa or N/m$^2$)
$\rho$ is the specific gravity at one point (in kg/m$^3$)
$v$ is the speed of the fluid at one point (in m/s)
g is the acceleration of gravity (in N/kg or m/s$^2$)
z is the altitude (in m)

The constant of the Bernoulli relationship above is also called the "charge".

The hypotheses for using this relationship are in agreement with the hypothesis of an incompressible fluid (the ink) and the type of flow (non-rotational, that is to say a non-turbulent flow) encountered in a system such as that constituted of an ink jet printer.

In the Bernoulli relationship, viscous effects and head losses are negligible.

It may be observed that altitude is not a parameter to take into account: for the current line situated on the axis of flow through the orifice 22, there is no altitude effect, the altitude is constant at this point and may be set at 0.

Furthermore, it is possible to generalise the Bernoulli relationship by integrating viscous effects and head losses, but these are negligible. In addition, it is possible to replace the speed by the flow rate (which is a similar parameter, the speed being the flow rate divided by the passage section S of the restriction 22: $v=Q/S$ and $S=\pi*D*D/4$, where D is the diameter of the orifice of the restriction 22).

Thus the pressure difference between the inlet and the outlet of the system may be written (equation (1)):

$$Pin-Pout=\alpha\cdot\rho\cdot q^2+\beta\cdot\mu\cdot q$$

With:
$P_{in}-P_{out}$: Pressure difference between the inlet and the outlet of the system
$\alpha$: Singular head loss coefficient
$\rho$: Specific gravity of the fluid
q: Flow rate traversing the system
$\beta$: Regular head loss coefficient
$\mu$: Dynamic viscosity of the fluid The resolution of this second degree equation (with respect to the flow rate) gives the following result:

$$q=-\frac{\beta\cdot\mu}{2\cdot(\alpha\cdot\rho)}+\sqrt{\left(\left(\frac{\beta\cdot\mu}{2\cdot(\alpha\cdot\rho)}\right)^2+\frac{(Pin-Pout)}{\alpha\cdot\rho}\right)}$$

This relationship makes it possible to calculate the flow rate q (or the speed of the jets).

Aspects concerning knowledge of the different parameters of this relationship will be discussed below.

As regards the characteristics of the ink ($\rho$, $\mu$), for a given fluid (here: ink or solvent) the values of the characteristics of the fluid are measured experimentally and for example given in the form of a table of values or graph, which may be memorised and supply data useful during the calculation.

Figure 5A:
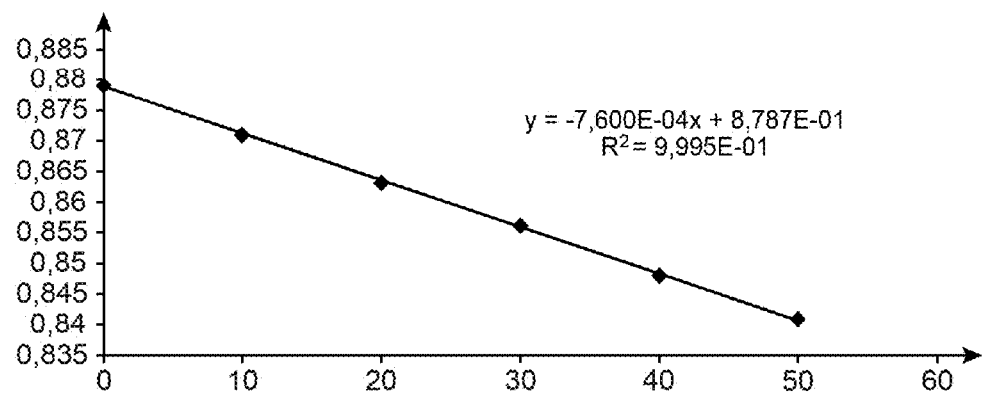
FIGS. 5A-5B are curves that illustrate the change, respectively of the density and the viscosity of an ink, as a function of temperature.
Figure 5B:
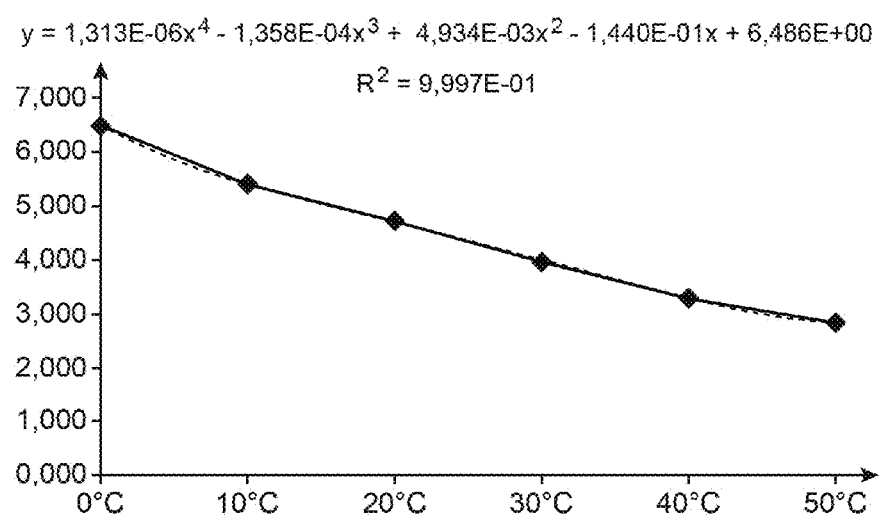

The examples of FIGS. 5A and 5B are relative to an ink and give in graphic form the density (the values given by FIG. 5A may be multiplied by 1000 to have the value of $\rho$ in legal units) and the viscosity $\mu$ in Centipoises (the values given by FIG. 5B may be divided by 1000 to have legal units).

For a temperature of 20° C., the specific gravity is 863 Kg/m$^3$ and the viscosity is 4.74 Cpe.

It may be seen in this example that the density of the ink changes in a decreasing but slight manner over the temperature range considered (for example between 0° and 50° C.), whereas the viscosity also changes for its part in a decreasing manner, but much more considerably, over this same temperature range.

In the case where the circuit for supplying with ink, or a device according to the invention, is provided with a viscometer (for example a falling ball viscometer (which measures the falling time of a ball), or a viscometer for measuring a transfer time through a viscous leakage), the viscosity value supplied by the latter may be used.

Means, for example such as those described hereafter, may be provided to carry out a control (or servo-control) of ink quality, while enabling the viscosity set point to be maintained at, for example, ±1 Cpe.

For specific gravity (or volumetric mass density or density, in kg/m$^3$ for example), which varies in a proportion much less than viscosity, the use of data from measurements carried out in the laboratory and presented for example in the form of a table of values or a graph may be sufficient for the range of use (0° C.-50° C.).

As regards the measurement of Pin–Pout, it is carried out by integrating, preferably, the offset or the generalised offset as already explained above.

The measuring chain may be equipped with a converter making it possible not to affect the resolution of the measurement. Typically a 16 Bit converter will be easily sufficient for the desired precision.

For example, for pressure measurements that can go up to 5 bars, a 16 Bit converter leads to a resolution error of 0.076 mb on the measurement of (Pin–Pout): a 5 bar coding on 65536 points leads to a resolution of 5000/65532=0.076 mbar; for ($P_{in}-P_{out}$) this error is counted twice, i.e. a resolution error on this measurement of 0.15 mbars. The typical value of ($P_{in}-P_{out}$) being of the order of 100 mbars, the resolution error, in %, is: 0.15%.

As regards the knowledge and the determination of ($\alpha$, $\beta$), it is possible to use equation (1) above, the pressure difference ($P_{in}-P_{out}$) between the inlet and the outlet of the system being this time known by measurement, in the same way as $\rho$, q and $\mu$, the values to determine being $\alpha$ (singular head loss coefficient) and $\beta$ (regular head loss coefficient):

$$(Pin-Pout)/q=\alpha\cdot\rho\cdot q+\beta\cdot\mu$$

By observing that by dividing the two terms of the equation by the flow rate q the equation becomes linear and it is seen that ($P_{in}-P_{out}$)/q may advantageously be plotted as a function of q.

2 points with separate flow rates may suffice to determine the coefficients, nevertheless the curve may advantageously be plotted with several flow rate values around the nominal flow rate.

Figure 6:
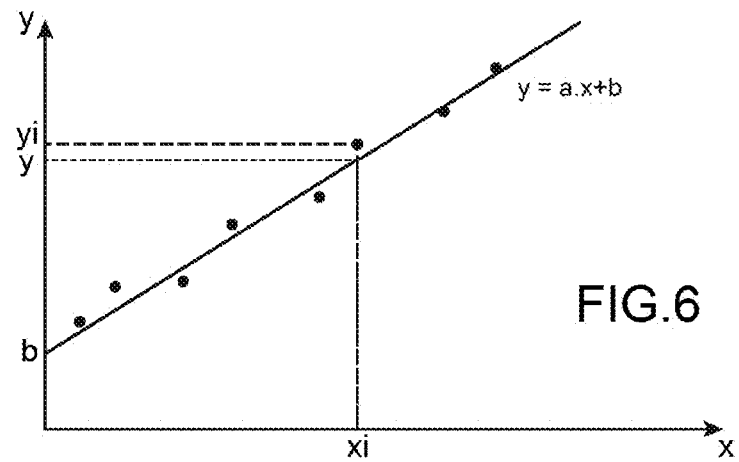
FIG. 6 represents the result of experimental measurements that make it possible to determine the singular and regular head loss coefficients for a flow meter according to the invention.

Knowledge of several points advantageously enables the use of a linear regression that makes it possible to determine:

a) The intercept, i.e. $\beta \cdot \mu$; by dividing this value by the known value of the viscosity, the coefficient $\beta$ is obtained;

b) The slope of the line, i.e. $\alpha \cdot \rho$; by dividing this value by $\rho$, (known value of the density), the coefficient $\alpha$ is obtained;

An example of curve, obtained by regression from measured values, is given in FIG. 6.

In addition, a correlation coefficient (absolute value close to 1) may be used to assess the quality of the adjustment.

An example of device that makes it possible to measure the coefficients $\alpha$ and $\beta$ is described hereafter.

This thus gives, with the values of $\rho$, $\mu$, $\alpha$ and $\beta$, an example of possible calculation of the flow rate. The values of $\rho$, $\mu$, $\alpha$ and $\beta$ may be memorised. The difference ($P_{in}-P_{out}$) is measured, with preferably correction of the offset or the generalised offset. The calculation of the flow rate q (or the speed of the jets) is deduced therefrom, using the formula above, which may also be memorised. All the calculations may be carried out by the controller of the printer.

Figures 7A, 7B:
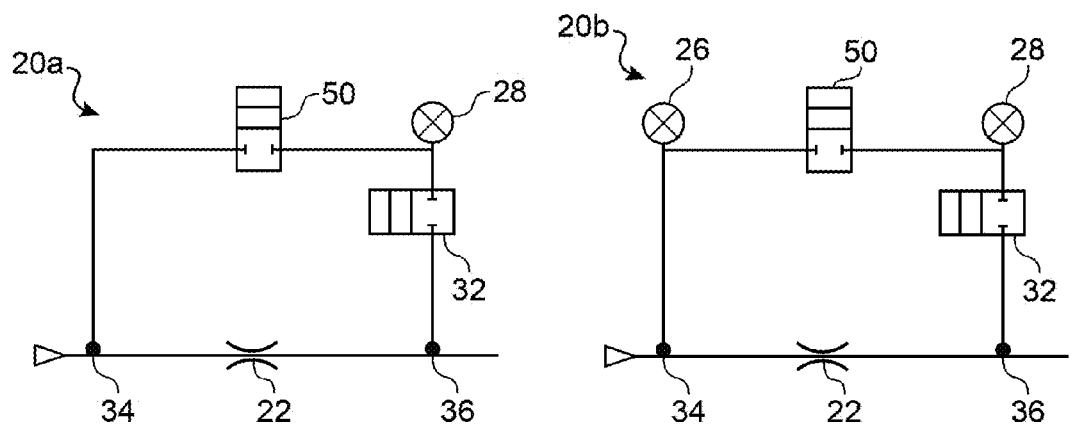
FIGS. 7A-7C are other exemplary embodiments of a flow meter according to the invention, for a circuit for supplying with ink a print head of an ink jet printer.

A variant 20a of a device according to the invention is illustrated in FIG. 7A. A single pressure sensor is used, for example the sensor 28 above. The means 30 and 32, arranged on either side of the sensor, alternatively enable a measurement of the pressure $P_{in}$ upstream of the orifice and a measurement of the pressure $P_{out}$ downstream of the orifice: when 30 is closed and 32 open, the pressure measured is that downstream of the orifice 22, when 30 is open and 32 closed, the pressure measured is that upstream. But the means 30, 32 are then more frequently called upon than in the embodiment explained above in relation with FIG. 3. Once again, it is possible to carry out cleaning or purging sequences, as explained above. With a single sensor, no offset compensation needs to be carried out, in particular if the measurements are made at practically constant temperature. The pressure differences between Pin and Pout are then exploited in the same way as that which is explained above for the calculation of the flow rate q. But since the measurements of $P_{in}$ and $P_{out}$ are not made at the same instant, a perturbation effect may exist to take into account, which is linked to the fluctuation of the working pressure.

Another variant 20b of a device according to the invention is illustrated in FIG. 7B, which can notably be used in the case where the problem of offset, generalised or not, is not posed or instead is negligible. A single means 30 is then used. The sensors 26 and 28 being arranged on either side of these means 30 to enable a simultaneous measurement of the pressure $P_{in}$ upstream of the orifice and a measurement of the pressure $P_{out}$ downstream of the orifice: when 30 is closed, the measured pressures are those downstream and upstream of the orifice 22. Once again, cleaning or purging sequences may be carried out, as explained above. The pressure differences between $P_{in}$ and $P_{out}$ are then exploited in the same way as that which is explained above for the calculation of the flow rate q.

Figure 7C:
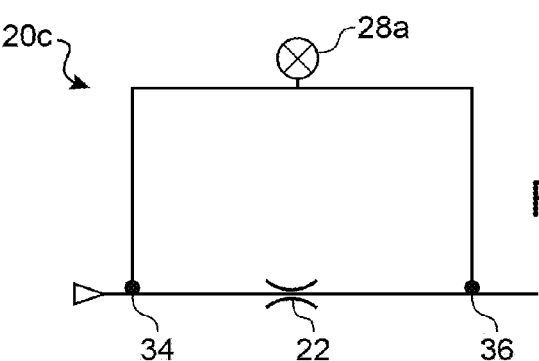

Yet another variant 20c of a device according to the invention is illustrated in FIG. 7C. A single pressure differential sensor 28a is used, without means 30 and 32. It gives directly a measurement of the pressure difference $P_{in}-P_{out}$. This type of device does not make it possible to correct the errors that result from an offset, it is thus possible to measure said offset before any use. The pressure difference $P_{in}-P_{out}$ directly measured is then exploited in the same way as has been explained above for the calculation of the flow rate q.

A flow meter 20, 20a-20c as described here is preferably integrated in the print head. But, for reasons of bulk (for example the limited miniaturisation of hydraulic components) it may be positioned on the ink supply line, upstream of the head in the supply circuit. An embodiment of such a flow meter has for example a volume of 50 mm×40 mm×30 mm.

Figure 2:
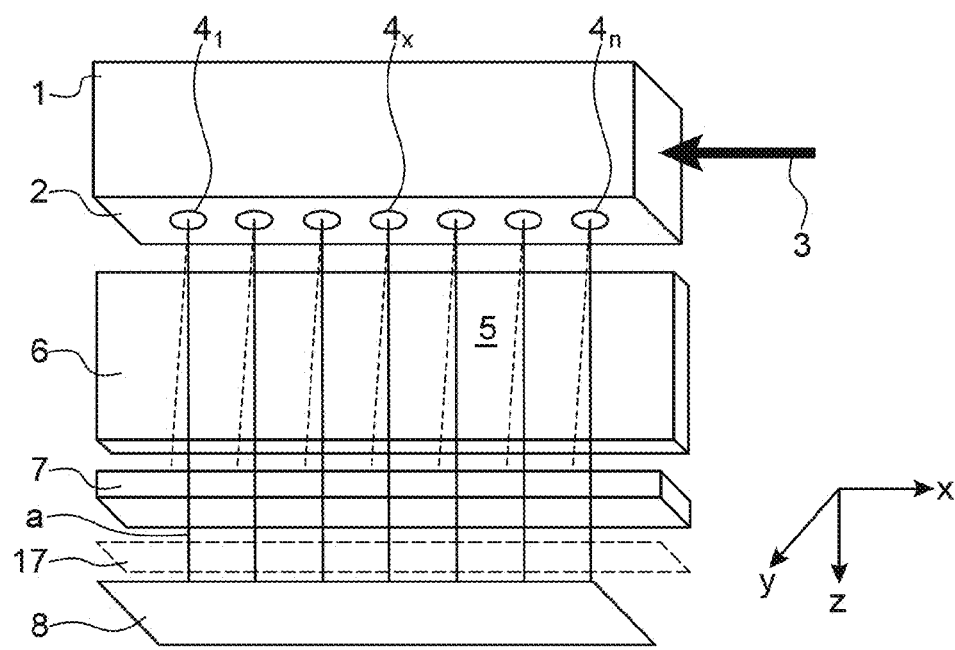
FIG. 2 represents a schematic cavalier view of a print head mainly revealing the components of the print head situated downstream of the nozzles.
Figure 3B:
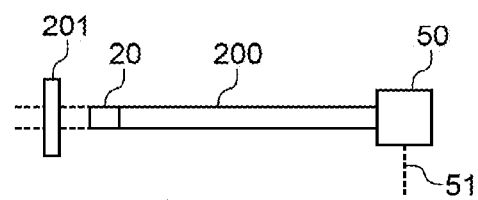
FIG. 3B is an exemplary embodiment of a conduit or umbilical for supplying with ink a print head of an ink jet printer, provided, at one end, with a flow meter according to the invention.

In FIG. 3B is schematically represented the flow meter 20 (which could, in a variant, be of the type 20a, or 20b, or 20c), at the inlet of the conduit or umbilical 200, of which the outlet is connected to a multi-jet print head 50 (which produces ink jets 51), the structure of which is for example of the type described above in relation with FIG. 2. A particular embodiment is given hereafter, in relation with FIGS. 8 and 9. The umbilical has a certain flexibility, so as to be able to bring the print head to various positions. The umbilical has for example a length comprised between 1 m and 8 m.

In order to ensure efficient protection of the calibrated orifice 22, the flow meter is preferably positioned downstream of the main filter 201 of the ink circuit.

A use has been described above of a flow meter 20, or one of its variants 20a-20c according to the invention, within the scope of an industrial ink jet printer. This flow meter makes it possible to measure, in an overall manner, the flow rate of the set of jets (for example in number greater than or equal to 16, or 64, or 128 jets) and is particularly suited when the individual speed of each jet is not known.

The calculation of the flow rate presented above may implement the viscosity value.

But such a flow meter may be combined with a pressure sensor preferably arranged in the print head, to form an assembly making it possible to measure both flow rate and viscosity.

Figure 8:
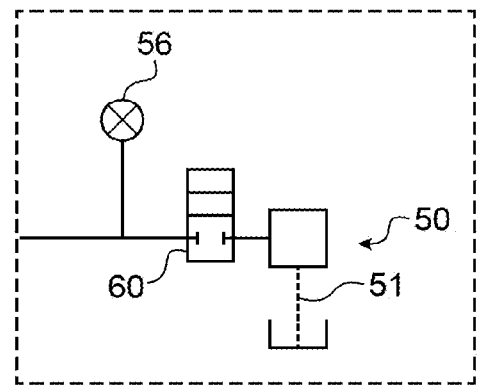
FIG. 8 is an exemplary embodiment of a print head according to the invention, for an ink jet printer.

In FIG. 8 is a diagram of a print head 50, which comprises a set of ink ejection nozzles. In a variant, the print head 50 may comprise a single ink ejection nozzle (for example for an application of CIJ type).

In the configuration illustrated, an electromagnetic valve 60 with two orifices (inlet and outlet) and two positions (open or closed) enables the passage (or stoppage) of fluid to the drop generator. This electromagnetic valve is located in the print head, near to the ink ejection nozzles.

A pressure sensor 56 is situated in the head just upstream of the electromagnetic valve 60; this sensor makes it possible to provide a measurement of the operating pressure of the ink in the head.

A temperature sensor (not represented in FIG. 8) may further be provided, which makes it possible to measure the temperature T of the fluid.

The hydraulic circuit of the head comprises conduits for supplying the set of nozzles (which are calibrated orifices of small dimension through which the jets of ink come out). Coefficients ($\alpha$Head, $\beta$Head) express the hydraulic characteristics of this circuit.

In a device according to the invention, a flow meter according to the invention, of the type already described above in relation with FIGS. 3-7C, may be positioned upstream of the pressure sensor 56. As already mentioned, the flow meter 20, 20a-20c is preferably integrated in the print head.

The flow meter may be at an altitude different to the pressure sensor 56. Generally speaking, a relative difference in altitude between these 2 components does not need to be taken into account, in particular if this difference remains constant during the operation of the printer. For the device with measurement of the operating pressure at the level of the head, the difference in height is not a parameter: it can vary without affecting either the operating pressure measured at the level of the head or the operation of the flow meter because the values Pin and Pout undergo the same offset and thus their difference remains constant. On an ink jet printer, the difference in altitude between the flow meter 20 and the pressure sensor 56 is limited (two meters is a typical maximum difference in height value between the ink circuit and the print head).

As regards the position of the print head, all positions (vertical printing upwards, vertical printing downwards, horizontal) are possible without significantly altering the precision of the system. Several calibration sequences, described hereafter, potentially make it possible to cancel or limit errors generated by the position of the head (the origin of errors being the acceleration of gravity and the distance of positioning between the sensor 56 and the outlet of the nozzles).

Preferably, the difference in altitude between the sensor 56 and the nozzles is as small as possible (typically less than five centimeters).

When the valve 60 is open a circulation of solvent makes it possible to clean the head. Moreover, a circulation of a liquid (solvent or ink) enables the evacuation of air (purging).

When the ink circuit is not pressurised, the sensor 56 can measure a pressure, which may have various origins (orientation of the head, and/or static errors of the sensor, etc.). An "offset" compensation may be carried out in different ways.

According to a $1^{st}$ method, a compensation at zero flow rate is carried out by opening the valve 60. Without pressurisation of the circuit the valve 60 is opened. The pressure sensor 56 sees the relative static pressure of the fluid (because it is a non-differential sensor, which measures the pressure compared to atmospheric pressure) as well as its own offset errors. The value announced by the measuring chain constitutes the "overall" offset (difference in height and specific offset of the sensor) and is going to be able to be used for any other measurement, which will thus be referenced at this offset measurement (Pressure=Pressure measured−Offset).

The static pressure of the fluid is thus compensated (which is the parasitic pressure generated by the column of fluid corresponding to the difference in height between the head and the ink circuit (or, preferentially, the flow meter). Conversely, the opening of the valve 60 may cause an inflow of air (if the head is situated at an altitude above the ink circuit) or lead to a low running of ink (if the head is situated at an altitude lower than that of the ink circuit). The error on the measurement of the offset, associated with the fact that the flow rate of fluid (linked to these runs) is not strictly zero (the pressure measured is then not perfectly static), is small, but there is a risk on the quality (directivity of the jets, establishment speed) of ink start-ups of the jets (on account of air inflows and/or runs).

According to a $2^{nd}$ method, the following are used:
a) the "offset" value at a given temperature: Offset (T0),
b) the offset drift as a function of temperature: dOffset.

These items of information may for example be obtained from the supplier of the sensor (who carries out an individual characterisation in air of each sensor) and may be stored in a memory associated with each sensor.

The compensation is carried out in the following manner:

Offset($T$)=Offset($T0$)+$d$Offset($T-T0$)

as soon as the temperature T is known.

This temperature (T) may be obtained thanks to a dedicated sensor. In fact, pressure sensors 56 exist that integrate a temperature measurement which enables, for a reduced cost, knowledge of T.

The advantages of this $2^{nd}$ method are, on the one hand, its ease of implementation associated with the fact that the compensation takes place by calculation (no specific sequence implementing components is necessary, thus the offset is calculated without any hydraulic perturbation of the circuit) and, on the other hand, the compensation may take place at any temperature.

But knowledge of the characteristics of the sensors may involve an extra cost. It may also be noted that the static pressure of the fluid is not compensated because the characteristic values are established in air and the position of the head influences this static pressure. Nevertheless the error generated by the position of the head (several mbars over the measured operating pressure) does not affect in a significant manner the expected precision. Finally, this compensation does not integrate errors (very small) associated with the measuring chain.

According to a $3^{rd}$ method, partial knowledge of the characteristics of the sensor is employed.

It is a variant of the $2^{nd}$ method, for which the offset at a given temperature is known, by a simple and inexpensive sequence carried out during the production of the machine. Indeed, the circuit is still in air; the pressure announced by the measuring chain is measured, this value constitutes the "offset" that will be applied to all later pressure measurements. Once again, this information may be stored in a memory associated with each sensor.

The advantages of this variant are its ease of implementation, associated with the fact that the compensation takes place by calculation (no sequence implementing components is necessary). And the measured "offset" value is indeed representative if the operating temperature is close to the temperature at which it has been measured.

The errors of the measuring chain (very small) are very well compensated at a temperature close to the temperature at which the offset has been measured during the production of the machine.

The flaws of this principle are the following:
the problem of drifts in temperature of the offset may be posed. It may thus be necessary to verify the drift values to ensure that the error generated does not affect in a significant manner the precision of the measurement,
it may also be noted that the static pressure of the fluid is not compensated because the characteristic values were established in air and the position of the head influences this static pressure. Nevertheless, the error generated (several mbars over the measured operating pressure) does not affect in a significant manner the expected precision;
finally, it is necessary to manage data for calibrating the head sensor during maintenance operations, including head exchanges.

According to a $4^{th}$ method, a compensation of the generalised offset ("offset" at the operating pressure) is employed. It is a variant of the $2^{nd}$ method, for which the characteristics of the sensor making it possible to compensate fully the errors associated with the sensor and with the variations in temperature are known.

This $4^{th}$ method makes use of the following four items of information concerning the characteristics of the pressure sensor with respect to its offset and its sensitivity:
Offset at a given temperature $T_0$: Offset ($T_0$).
Offset drift as a function of temperature: d Offset.
Sensitivity at a given temperature $T_0$: $S(T_0)$.
Sensitivity drift with temperature: dS.

These items of information may be obtained from the supplier of the sensor and may be stored in a memory associated with each sensor.

The relationship enabling the pressure (P) to be known as a function of the measurement (Measurement) and the temperature (T) is then:

$$P = \frac{Mesure}{S(T0) + dS*(T - T0)} - (\text{Offset}(T0) + d\ \text{Offset}(T - T0))$$

Figure 9A:
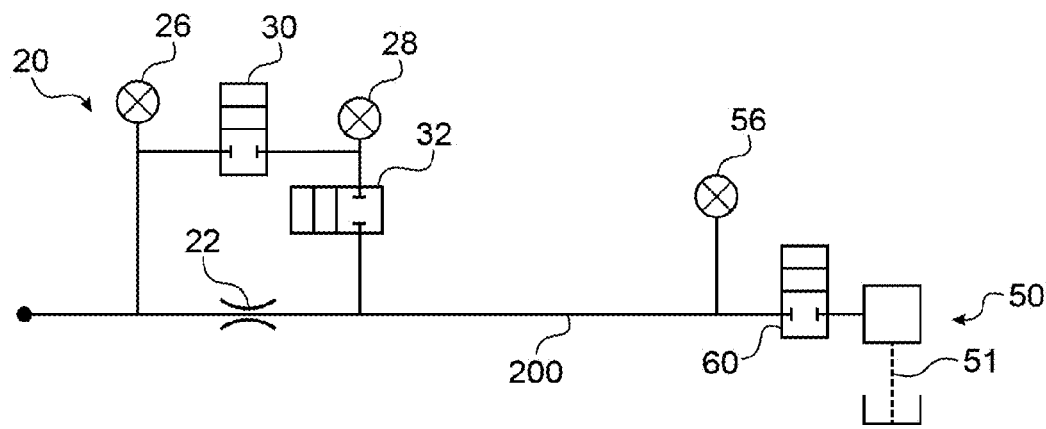
FIG. 9A is an exemplary embodiment of an assembly comprising a flow meter according to the invention and a print head according to the invention, for an ink jet printer.

How the flow rate and the viscosity may be measured will now be described in greater detail, in relation with FIG. 9A, using a flow meter as described above and a print head as described above. The system of FIG. 9A comprises a flow meter according to one of the types described above (a flow meter 20 has been represented in this figure, but the system also functions with flow meters 20a-20c of the type of FIGS. 7A-7C).

The measurement may notably result from knowledge of the following parameters:
- the hydraulic characteristics of the orifice 22, more exactly the two coefficients α and β characteristic of the singular and regular head losses of the orifice;
- the physical characteristics of the fluid (ink), in fact the specific gravity (or volumetric mass density or density, in kg/m³ for example), and the viscosity of the fluid;
- the pressure difference between the inlet pressure (Pin) and the outlet pressure (Pout) when the valve 30 is closed and the valve 32 open;
- the operating pressure PHead measured by the sensor 56; potentially corrected for its offset.
- the hydraulic characteristics of the print head; more exactly the two coefficients αHead and βHead characteristic of the singular and regular head losses of the head.

Potentially, it is possible to take account of the offset, preferably generalised, of the flow rate sensor, corresponding to the pressure difference between the inlet pressure (Pin) and the outlet pressure (Pout) when the valve 30 is open and the valve 32 closed. The generalised offset useful to obtain the desired precision is then measured, as already explained above.

Potentially, it is possible to take account of the offset of the sensor 56, the operating pressure P Head then being corrected for this offset, measured as already explained above.

The equations that model the system are the following:

$$P\text{in}-P\text{out} = \alpha FI \cdot \rho \cdot q^2 + \beta FI \cdot \mu \cdot q$$

$$P\text{Head} = \alpha \text{Head} \cdot \rho \cdot q^2 + \beta \text{Head} \cdot \mu \cdot q$$

Pin–Pout, P Head, q, ρ, μ, α, β, αHead and βHead each have the signification already given above.

The conventional resolution of these two equations with two unknowns (flow rate and viscosity) leads to:

$$q = \sqrt{\frac{(P\text{ Head} * \beta FI - (P\text{in} - P\text{out}) * \beta \text{ Head})}{(\rho * (\alpha \text{ Head} * \beta FI - \alpha FI * \beta \text{ Head}))}}$$

$$\mu = \frac{((P\text{in} - P\text{out}) * \alpha \text{ Head} - (P\text{ Head} * \alpha FI))}{(\alpha \text{ Head} * \beta FI - \alpha FI * \beta \text{ Head})} \Bigg/ \sqrt{\frac{(P\text{ Head} * \beta FI - (P\text{in} - P\text{out}) * \beta \text{ Head})}{(\rho * (\alpha \text{ Head} * \beta FI - \alpha FI * \beta \text{ Head}))}}$$

Aspects are discussed below concerning knowledge of the different parameters of this relation, Pin–Pout, ρ, μ, α and β, and the corresponding methods of determination, having already been discussed above.

As regards the operating pressure P Head, this is obtained by acquisition of the signal delivered by the pressure sensor 56. The gross value delivered by the sensor may moreover be corrected for the offset, as explained above.

As regards the hydraulic characteristics (αHead, βHead), the following operating equation (2) is used:

$$P\text{Head} = \alpha \text{Head} \cdot \rho \cdot q^2 + \beta \text{Head} \cdot \mu \cdot q$$

the parameters of which have already been described above, PHead, ρ, q and μ being known by measurement, the values to determine being αHead (singular head loss coefficient) and βHead (regular head loss coefficient):

By remarking that by dividing the two terms of the equation by the flow rate q the equation becomes linear it is seen that PHead/q may advantageously be plotted as a function of q.

Two points with separate flow rates may suffice to determine the coefficients, nevertheless the curve may advantageously be plotted with several flow rate values around the nominal flow rate.

Knowledge of several points advantageously enables the use of a linear regression which makes it possible to determine:

a) The intercept, i.e. βHead·μ; by dividing this value by the known value of the viscosity, the coefficient βHead is obtained;

b) The slope of the line, i.e. αHead·ρ; by dividing this value by ρ, the coefficient αHead is obtained.

In addition, the correlation coefficient (absolute value close to 1) may be used to assess the quality of the adjustment.

How the flow rate and the viscosity may be measured using an other device according to the invention will now be described in greater detail, in relation with FIG. 9B. Said other device comprises a print head 50, for example as described above (in relation with FIG. 8) and a flow meter 20d, which can of another type than those already described above, for example a flow meter with "Coriolis" or ultrasound or electromagnetic type effect. This flow meter 20d makes it possible to measure the flow of ink that is sent to the print head 50 via the conduit 200.

The measurement may notably result from knowledge of the following parameters:
- the physical characteristics of the fluid (ink), in fact the specific gravity and the viscosity of the fluid;
- the operating pressure PHead measured by the sensor 56;
- the hydraulic characteristics of the print head; more exactly the two coefficients αHead and βHead characteristic of the singular and regular head losses of the head.

Potentially, it is possible to take account of the offset of the sensor 56, the operating pressure P Head then being corrected for this offset, measured as already explained above.

The equation that models the system is then the following:

$$P\text{Head} = \alpha \text{Head} \cdot \rho \cdot q^2 + \beta \text{Head} \cdot \mu \cdot q$$

P Head, q, μ, μ, αHead and βHead each have the signification already given above.

The resolution of this equation (flow rate and viscosity) leads to:

$$\mu = (P\text{Head} - \alpha\text{Head} \cdot \rho \cdot q^2)/\beta\text{Head},$$

the flow rate q being measured with the flow meter 20d.

Means 70, 300, for example those disclosed in this application (see in particular FIG. 11) in connection with other embodiments, may be provided in combination with the embodiment disclosed in relation with FIG. 9D, for:
- calculating the viscosity of ink as a function of the pressure (PHead) measured by the pressure sensor, for example as a function of the hydraulic characteristics (αHead, βHead) of the print head, and the pressure measured by the pressure sensor;
- and/or for correcting, preferably as a function of temperature, a measurement difference, for at least one pressure, between a pressure value of the head measured by the pressure sensor and said actual pressure.

Figure 9B:
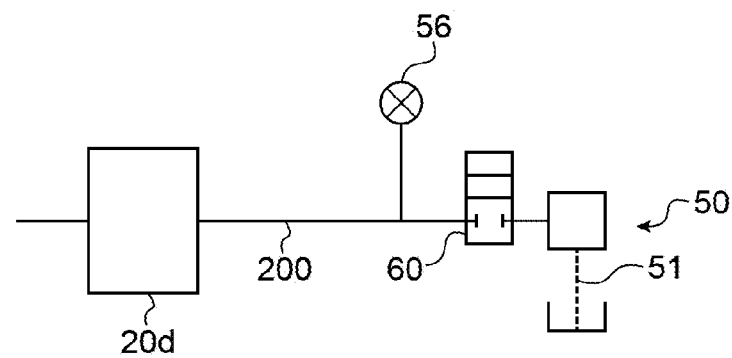
FIG. 9B is an exemplary embodiment of an assembly for measuring flow rate and viscosity, for an ink jet printer.

Other viscometer or means for measuring viscosity can be combined with flow meter 20d of FIG. 9B. In a variant, the means for measuring viscosity comprise a conduit 220 (as disclosed in relation to FIGS. 10A-10D), arranged in line or in series with the device for measuring ink flow rate (downstream or upstream therefrom), and means 28, 226, 228 (as disclosed in relation to FIGS. 10A-10D), for measuring a pressure difference (Poutv−Pinv) between an inlet and an outlet of said conduit 220. According to a particular embodiment, a same common sensor 28 makes it possible to measure:
- the pressure of ink downstream of the restriction and the pressure at the inlet of the conduit 220,
- or the pressure of ink upstream of the restriction and the pressure at the outlet of the conduit 220.

Figure 10A:
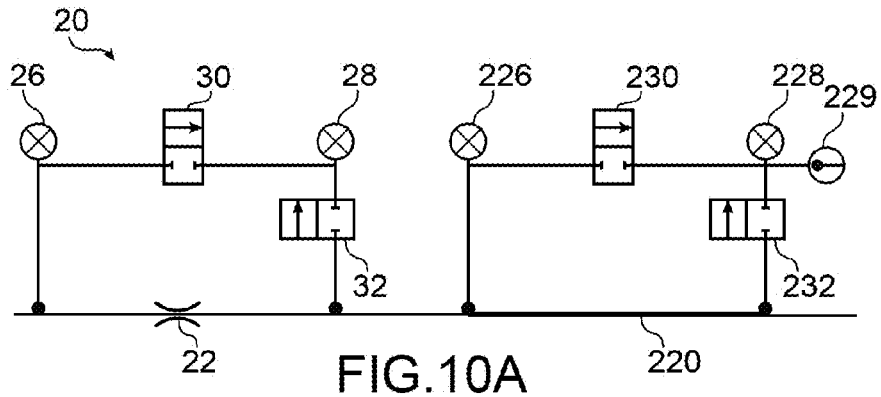
FIGS. 10A-10D are other exemplary embodiments of an assembly for measuring flow rate and viscosity, for an ink jet printer.

Any flow meter 20, 20a-20d, in particular as described above, may be combined with a flow conduit or a pipe 220 as illustrated in FIGS. 10A (and 10C). The flow conduit 220 is represented here downstream of the flow meter, but, in a variant, it could be upstream of the latter.

The aspects of cleaning, purging and offset compensation described above for the flow meter 20 also apply here.

At the ends of the conduit 220 (which is not the umbilical: it is sought in fact to know the viscosity without constraints linked to the umbilical and the head), are located a $1^{st}$ and $2^{nd}$ pressure sensor 226, 228, preferably with flush membrane with the advantages already described above. The pressures that they are going to make it possible to measure are designated, respectively, PinF and PoutF. The set of means 220 and 226-232 forms a viscometer.

In the embodiment illustrated, means or an element or an organ 230 for placing in fluidic communication the 2 sensors, preferably a valve or an electromagnetic valve, with two orifices (inlet and outlet) and two positions (open or closed), makes it possible to connect or to place in fluidic communication the two pressure sensors 226 and 228, that is to say to enable these 2 elements to be placed at the same pressure.

Means or an element or an organ 232 for placing in fluidic communication the sensor 228 and the outlet of the conduit 220, preferably a valve or an electromagnetic valve, with two orifices (inlet and outlet) and two positions (open or closed) makes it possible to connect or to place in fluidic communication the pressure sensor 228 with the outlet of the conduit 220. A circulation of fluid through the elements 226, 230, 228, 232 is used in the case of a purging of the system.

Figure 10B:
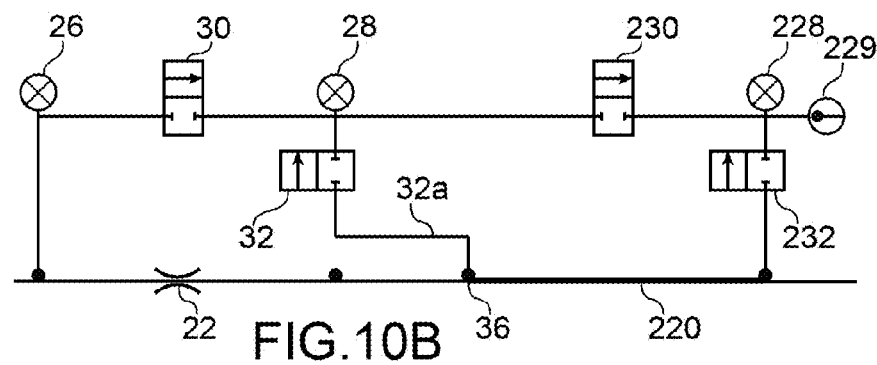
Figure 10C:
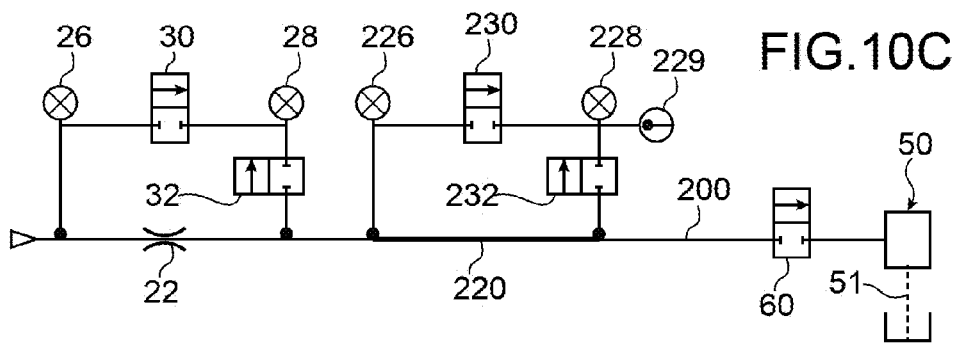

The flow rate of the fluid to measure traverses both the calibrated orifice 22 of the flow meter as well as the pipe, placed in series with the flow meter, and supplies the set of jets of the print head through the umbilical 200, as illustrated in FIG. 10C.

A temperature sensor 229 is arranged so as to measure the temperature T of the fluid in the circuit (upstream of the head), for example at the outlet of the sensor 228.

This assembly is going to make it possible to calculate the flow rate and the viscosity of the fluid.

In fact, as described above, the calculation is then limited to the resolution of two equations with two unknowns.

The pipe 220 forms a very long restriction in view of its diameter (for example 3 m for a diameter of 1.6 mm; more generally a ratio greater than 1000 between length and diameter will be taken. For example: L=3000 mm and d=1.6 mm; or instead: L=3000 mm and d=2.7 mm.

The conduit 220 forms a viscous leak; it forms means to create a pressure drop by friction loss; such means can be formed by means of a narrowing of a fluidic duct which is substantially longer than its diameter (which is the case of pipe 220), thus setting up a pressure drop sensitive to, or dependant on, the viscosity of the fluid circulating therein.

Figure 10D:
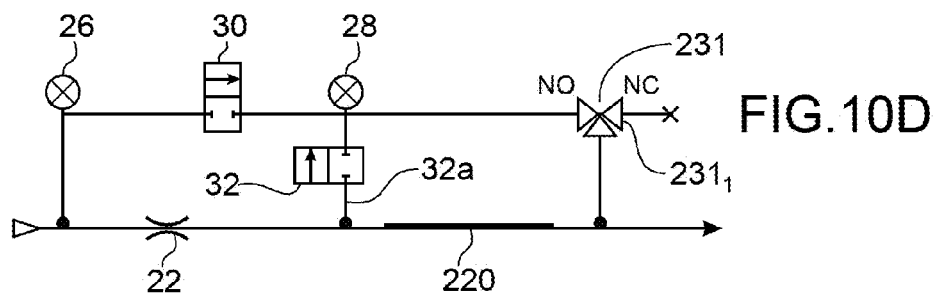

In this embodiment but also in the other embodiments, in particular those disclosed in relation to FIGS. 10B-10D, the conduit 220 forms a viscous leak; but, for dimensioning reasons, it can be replaced by a succession of viscous leaks, in series.

The measurement of the generalised offset of the assembly formed by the sensors 226 and 228 may be carried out in the same way as for the flow meter 20, already described above.

The measurement of the flow rate and the viscosity may notably result from knowledge of the following parameters:
- the parameters already presented above for the measurement of the flow rate (these parameters are designated, for this embodiment, αF and βF),
- the pressure difference (at the operating pressure) between the inlet pressure (PinV) and outlet pressure (PoutV) of the pipe 220 when the valve 230 is open and the valve 232 closed; it is then possible to measure the offset or the generalised offset to obtain the desired precision;
- the pressure difference (at the operating pressure), preferably corrected for the generalised offset, between the inlet pressure (PinV) and outlet pressure (PoutV) of the pipe 220 when the valve 230 is closed and the valve 232 is open, compared to the difference (PinV−PoutV);
- the hydraulic characteristics of the pipe 220; in fact a single coefficient βv characteristic of the regular head loss of the pipe suffices.

The equation (1) already presented above:

$$P\text{inF} - P\text{outF} = \alpha F \cdot \rho \cdot q^2 + \beta F \cdot \mu \cdot q$$

is here completed by the following equation:

$$P\text{inV} - P\text{outV} = \beta v \cdot \mu \cdot q \qquad (3)$$

in which the parameters have the signification already presented above.

This system is a system of two equations with two unknowns (flow rate and viscosity), the resolution of which leads to:

$$q = \sqrt{\frac{(\beta V * (PinF - PoutF) - \beta F * (PinV - PoutV))}{(\rho * \alpha F * \beta V)}}$$

And to:

$$\mu = \frac{(PinV - PoutV)}{\beta V} \Big/ \sqrt{\frac{(\beta V * (PinF - PoutF) - \beta Fl * (PinV - PoutV))}{(\rho * \propto Fl * \beta V)}}$$

Reference may be made to the explanations already given above as regards the measurement of PinF–PoutF as well as the knowledge and the determination of the coefficients αF and βF.

In a variant, for the determination of αF and βF, the quadratic relationship (1) above may be kept; this second principle of determination of αF and βF is more suited than the first. It makes it possible in particular to better apprehend the quality of the measurements.

In this case, obviously, two points with separate flow rate suffice to determine the coefficients; nevertheless it is advisable to plot the curve with numerous flow rate values surrounding the nominal flow rate. And knowledge of numerous points advantageously enables the use of a regression The coefficient of the flow rate q (βF·μ) is then obtained; by dividing by the known value of the viscosity, the coefficient βF is obtained.

The coefficient of the flow rate q², which is nothing other than αF·ρ; by dividing by ρ the coefficient, αF is obtained.

In addition, a correlation coefficient (absolute value close to 1) may be used to assess the quality of the adjustment.

The intercept (value of the equation given by the regression when q=0) may also be used to assess the quality of the adjustment.

As regards the measurement of PinV–PoutV, it is preferably carried out by integrating the offset or the generalised offset.

The measuring chain may be equipped with a converter making it possible not to affect the resolution of the measurement. Typically a 16 Bit converter will be largely sufficient for the desired precision.

In these conditions, and as already explained above for the measurement of Pin–Pout, the typical value of (PinV–PoutV) being of the order of 100 mbars, the resolution error, in %, is: 0.15%.

For the determination of the coefficient βV, the following equation is used:

$$PinV - PoutV = \beta V \cdot \mu \cdot q.$$

The relation being linear, βV may be determined with 2 approaches (calculations with uniquely 2 points or linear regression).

Two points with separate flow rates may suffice to determine the coefficient, nevertheless, the curve may advantageously be plotted with several flow rate values around the nominal flow rate.

Knowledge of several points advantageously enables the use of a linear regression, which makes it possible to determine the slope of the line, i.e. βV·μ; by dividing this value by μ (known value of the viscosity), the coefficient βV is obtained.

In addition, it is possible to use a correlation coefficient (of absolute value close to 1) to assess the quality of the adjustment.

It is also possible to assess the quality of the measurements by evaluating the intercept (which groups together the errors of principle and measurement).

An example of device which makes it possible to measure the coefficients αF, βF and βV is described hereafter.

In a variant, represented in FIG. 10B, it is possible to simplify the circuit using a same pressure sensor for measuring PoutF and PinV (in fact, it then involves a same pressure Pout/in) and while keeping a line 32a and the means 32 between, on the one hand, the outlet point of the flow meter (which is also the inlet of the viscometer) and, on the other hand, the common sensor 28 (for measuring Pout/in), situated between the valves 30 and 230.

If the viscometer is placed upstream of the flow meter, these 2 devices may have common sensors 26 and 228; this configuration is not represented here.

Generally speaking, for questions of precision, it is preferable to use a device in which the flow meter and the viscometer do not have a common sensor (configuration of FIG. 10 A, or configuration in which the viscometer is upstream of the flow meter).

For the determination of the generalised offsets in the configuration of FIG. 10B, the means 30 and 230 are opened while closing the means 32 and 232 when the pressure is applied to the circuit without flow rate; the real pressure is then identical on the 3 pressure sensors 26, 28, 228. The measured pressure differences enable the necessary offsets to be determined.

For the cleaning and the purging of this variant of FIG. 10B, the operation takes place in 2 phases:
  the means 30 and 32 are open, the means 230 and 232 being closed;
  then the means 30 and 32 are closed, the means 230 and 232 being open.

In normal operation: the means 32 and 232 are open, the means 30 and 230 being closed.

Finally, in the equations, PoutF and PinV are replaced by Pout/in.

In a variant, represented in FIG. 10D, it is possible to simplify the circuit even further by using a single pressure sensor 28 for measuring PoutF and PinF and while keeping a line 32a and the means 32 between, on the one hand, the outlet point of the flow meter (which is also the inlet of the viscometer) and, on the other hand, the common sensor 28, situated between the valves 30 and 230. The outlet sensor 228 is done away with.

In this embodiment:
  to measure the pressure at the inlet of the conduit 220, the valves 30 and 231 are closed and the valve 32 is open;
  to measure the pressure at the outlet of the conduit 220, the valves 30 and 32 are closed and the valve 231 is open.

The valves or electromagnetic valves 30, 32, 230, 232 of FIGS. 10A-10C are normally closed. They are open when activated.

This variant illustrated in FIG. 10D is more economical; it moreover makes it possible to protect the sensor 28 when the printer is stopped. It makes use of a valve 231, preferably 3 way valve, which is normally open and closed when activated. It could also be a 2-way valve which is normally open (and closed when activated) but usually, most of the 2-way valves are normally closed (and open when activated).

This variant makes it possible to use only one sensor (the sensor 28) for measuring alternatively the pressure on either side of the viscous leakage 220 with an appropriate sequencing of the valves: since the variation in viscosity has a much longer response time than that of the variation in flow rate, the pressure measurements linked to the viscosity are less sensitive to pressure fluctuations (these measurements may be significantly averaged); therefore, not performing a simultaneous measurement of the pressure on either side of the restriction will not affect the precision very much.

This variant has the advantage that a sensor (sensor 228 of FIG. 10B) and 2 valves (230 and 232 on FIG. 10C) are replaced by a single 3-way valve 231, which is normally open.

It also offers the possibility to protect sensor 28: when printing is stopped, sensor 28 is at atmospheric pressure, like the other sensor 26; it is not "locked" or blocked between several valves (see valves 30, 32, 230 of FIG. 10B) which are normally closed, with a risk of being subject to a residual pressure or an excessive pressure due for example to variations of temperature. When printing is stopped valve 231 is normally open, and therefore sensor 28 is at atmospheric pressure. The other outlet $231_1$ of valve 231 is closed.

This device can be easily connected to a test bench in order to calibrate it; the printer therefore does not need specific calibration means. After calibration it can be mounted in a printer. And the measurements obtained when implementing this device are independent of altitude variations.

The variants of FIGS. 7A-7C are applicable to the configurations of FIGS. 10 A-D. In other words, a flow meter as described in relation with one of FIGS. 7A-7C may be used in combination with a viscometer described above in relation with FIG. 10A or 10D.

Figure 1:
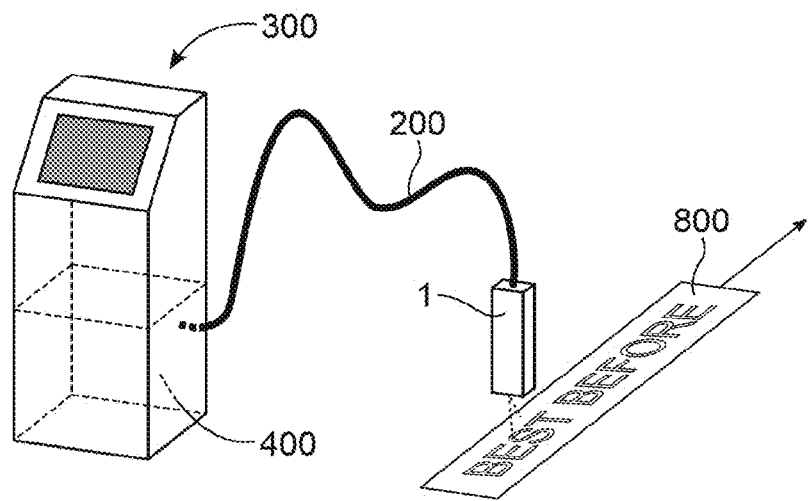
FIG. 1 is a perspective view of an ink jet printer known from the prior art.

A flow meter, in particular as described above, and/or a head according to the invention may be implemented in a printer such as that described above in relation with FIG. 1. This comprises notably a print head 1 (or 50), generally offset with respect to the body of the printer 300, and connected thereto by means, for example in the form of a flexible umbilical 200, grouping together the hydraulic and electrical connections enabling the operation of the head. The umbilical 200 may incorporate a flow meter as explained above (see FIG. 3B).

The body 300 comprises means forming controller or control means.

The latter comprise for example a micro-computer or a micro-processor and/or an electronic or electric circuit, preferably programmable, which is going to transmit printing instructions to the head but also control the means or the hydraulic elements of the system for supplying with ink and with solvent, notably the solvent and/or ink pumps and/or the valves of the system, in particular the valves 30, 32, 60, in order to manage the supply of the circuit with ink and/or with solvent as well as the recovery of the mixture of ink and solvent from the head.

This controller or these control means can also collect items of information on pressure or pressure differences supplied by the sensors 26, 28, 28a, 56, or by the flow meter 20d, potential items of information on temperature, and calculate or estimate the flow rate and/or the viscosity of the ink. It may also carry out one or several offset corrections, as explained above. This controller or these control means may also:

command the sending of solvent, in order to adapt the viscosity of the ink in the circuit;
command a pump for pressurising the ink, in order to adapt the flow rate.

The controller or the control means are thus programmed depending on the functions that have to be managed in the printer.

A device according to the invention may be incorporated in a system for controlling or servo-controlling at least one operating parameter of an ink jet printer. Compared to one or several set points of this (or these) parameter(s), for example flow rate and/or viscosity, a device according to the invention makes it possible to calculate or estimate one or several differences, which may be corrected or reduced using means for controlling or servo-controlling this (or these) parameter(s).

More particularly, the combination of a flow meter and a pressure sensor (or a viscometer as described above, in particular in relation with FIGS. 10A-10D) as above enables 2 controls or servo-controls to be made:

a) a control (or servo-control) of the speed of the jets. For a multi-jet printer the overall flow rate of the jets is used as control parameter, the flow meter may thus form the sensor of the flow rate control loop, b) a control (or servo-control) of ink quality. It is possible to a control (or servo-control) the concentration of the ink, or the viscosity. The use of the flow meter coupled with a sensor of the operating pressure (or with a viscometer as described above, in particular in relation with FIGS. 10A-10D) makes it possible to know the viscosity of the ink (as well as the overall flow rate of the jets).

A flow meter and a sensor of the operating pressure (or a viscometer as described above, in particular in relation with FIGS. 10A-10D) described above may be implemented in an control or servo-control system according to the invention, forming sensors of one or more control loop(s) implemented in a multi-jet printer.

The data provided by these sensors are linked: knowledge of the viscosity enables the flow meter to be precise and knowledge of the flow rate makes it possible, through the operating pressure, to determine correctly the viscosity of the fluid.

The two control loops are thus linked.

Preferably, the servo-control or control of flow rate is priority, with a typical response time of the order of a second: the time difference between a modification of a parameter of the circuit (for example the speed of a pump) to modify the flow rate and the actual modification of the flow rate of the jets is less than or equal to 1 s. The management of ink quality through the servo-control of the viscosity is less priority and less rapid, a response time of the order of a minute being sufficient: the time difference between a modification of a parameter of the circuit (for example the opening of a valve for supplying with solvent) to modify the viscosity and the actual modification of the viscosity of the ink of the jets is around 1 min, or less than or equal to 1 min, or comprised between 30 s and 2 min.

Figure 11:
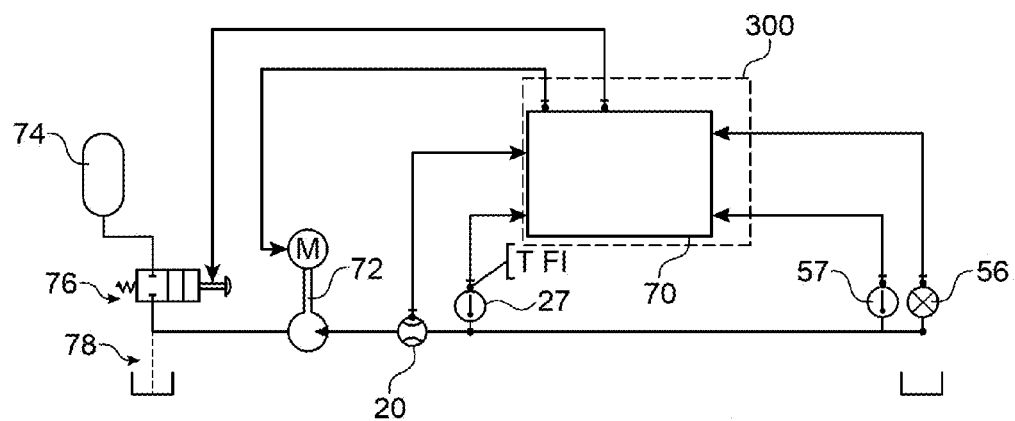
FIG. 11 is an exemplary embodiment of a flow rate and/or viscosity control or servo-control system according to the invention, for an ink jet printer.

As illustrated in FIG. 11, a central computer 70 (for example the controller of the printing machine) may be used to ensure these controls or servo-controls. This may form part of the controller or control means, in the body 300 of the printer.

The data in the memory of the computer may be the following:

a) The hydraulic characteristics $\alpha$ and $\beta$ (or $\alpha F$ and $\beta F$) of the flow meter;

b) The hydraulic characteristics $\alpha$Head and $\beta$Head of the head (or the hydraulic characteristic $\beta V$ of the viscosimeter as described above, in particular in connection with FIGS. 10A-10C), c) The characteristics $\rho$ and $\mu$ of the ink, for example measured in the laboratory.

For a device as on FIG. 9B, the data in the memory of the computer may be the following:

d) The hydraulic characteristics $\alpha$Head and $\beta$Head of the head;

e) The characteristics $\rho$ and $\mu$ of the ink, for example measured in the laboratory.

The input data of the computer may be the following:

a) The pressure difference (Pin−Pout or PinF−PoutF), supplied by the flow meter 20, or 20a-20c or the flow measurement provided by flow-meter 20d;

b) The temperature TFi of the ink in, or near to, the flow meter (measured using the temperature sensor 27, potentially integrated with one of the pressure sensors), c) The operating pressure P Head, provided by the sensor 56 or the pressure difference PinV−PoutV of the viscosimeter, d) The temperature of the ink in the head (T Head, measured using the temperature sensor 57, potentially integrated with the pressure sensor 56), or in the viscosimeter (measured with sensor 228);

e) A flow rate set point (which may be constant); this set point may be stored in a memory of the computer 70, f) A viscosity set point of the ink, which may be temperature dependent; this set point may also be stored in a memory of the computer 70.

The output data of the computer 70 are for example:

a) data for controlling the motor of a pump 72 for pressurising the ink circuit, with a view to a variation in the speed of this motor, b) and/or data for commanding an electromagnetic valve 76, with a view to addition of solvent into the circuit, from a solvent cartridge 140, for example via a circuit in part identical to the circuit for sending ink to the head.

With the memorised data and the input data, the computer 70 may (for example with the calculations already explained above) estimate or calculate the flow rate (or the speed) and/or the viscosity of the ink. The pressure data are preferably corrected for their offset.

For the control of the flow rate, a proportional type control or servo-control is suited. It is possible to take into account an integral term. The gain, which makes it possible to transform the difference in flow rate observed into difference in speed of the motor of the pump 72, may for example be obtained by measurements carried out on a representative set of machines. It is preferable to give greater importance to the precision than to the rapidity of the servo-control by choosing a gain not having a risk of servo-control pumping (rapidity is often a source of exceeding the target value, a system that reacts rapidly being able to find itself below the latter and to do so on several occasions; this is known as "pumping").

For the control of the viscosity, a proportional-integral type control or servo-control is suited. From the practical point of view, the gain in the control or servo-control (proportional term and integral term) may be obtained in an experimental manner.

The addition of a derived term (translating the trend to deviate from the set point: either one approaches the set point or the target value and the trend or the slope is negative, or one moves away from the set point or target value and the trend or the slope is positive) is possible, but of limited interest. In fact, an advantage of this measurement system, giving viscosity and flow rate, is to benefit from a continuous (or practically continuous) measurement of the viscosity, for example with a difference of a second (or more) between 2 consecutive measurements. The fact of benefiting from a continuous, or very frequent, measurement, makes it possible:

to modulate and adapt a volume of solvent to add, to monitor a servo-control from filtered or averaged viscosity values; in fact, in a CIJ printer equipped with a flow time measurement viscometer, a viscosity measurement value is only available around every 8 minutes and it is possible to ensure correct servo-control of ink quality. By having available a measurement value frequently, for example each second, it is possible to treat the measured values (for example by calculation of an average, and/or by filtering, etc.), by means for calculating an average or by a filter.

to be able to monitor the effects of additions of solvent on a printer having a quicker response time than a CIJ type printer. In fact the response time of a printer is mainly associated (all other things being equal) with the transfer time of the ink from the ink reservoir (in which it is stored) to the print head (in the places where the effects of the viscosity of the ink are visible). A simple calculation makes it possible to evaluate the ratio of the response times between a binary multi-jet type printer and a CIJ printer (single jet or twin jet).

For example, by making the following hypotheses:

identical lengths of umbilical between the two types of printers, inner diameter of the pressure pipe of a binary multi-jet type printer: 2.7 mm; inner diameter of the pressure pipe of a CIJ type printer: 1.6 mm, flow rate of the jets for a binary multi-jet type printer 3.1 l/h; flow rate for a CIJ type printer: 0.24 l/h, On the basis of these hypotheses, this gives a ratio of the response time (binary multi-jet/CU)=$(1.6/2.7)^2 \times 3.0/0.24$=4.5.

It is possible to verify experimentally the response of the flow rate and viscosity controls or servo-controls:

1) to an instantaneous difference, that is to say the response to a step function, for example to a difference of 10% compared to a so-called nominal flow rate value, 2) and/or to a viscosity difference, for example a difference of 1 Centipoise, 3) and/or to a temperature ramp, for example comprised between 0° C. and 50° C. with a slope of 5° C./h.

A measurement of the flow rate or speed of the jets and/or viscosity according to the invention, and potentially a control or servo-control of the pressure and/or the viscosity as explained above, may be carried out during printing of a multi-jet ink jet printer.

Figure 12:
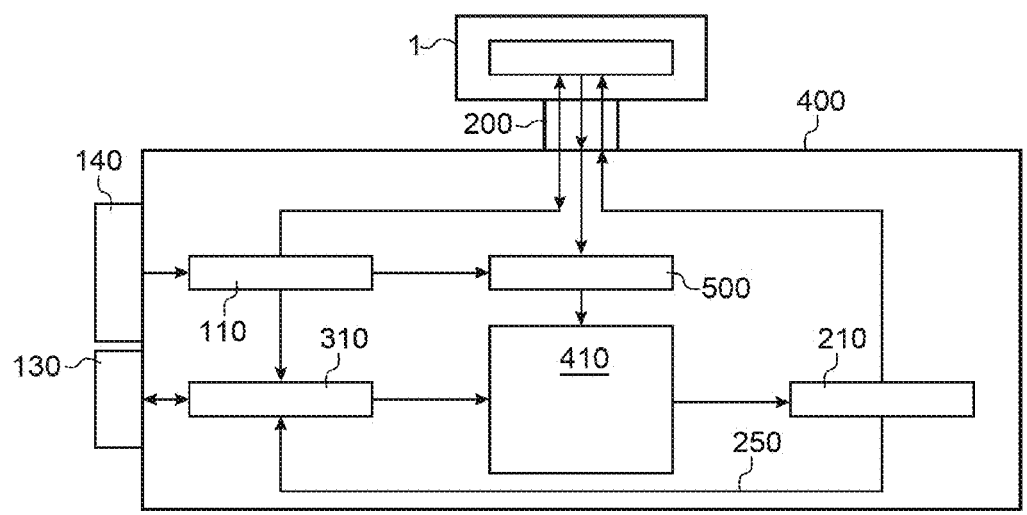
FIG. 12 represents an example of fluidic circuit structure to which the invention may be applied.

What has been described above, for example the system described in relation with FIG. 11, may be applied to an example of architecture of the fluidic circuit of a printer as illustrated in FIG. 12.

An example of architecture of the fluidic circuit of a printer to which the various aspects of the invention may be applied, individually or in combination, is illustrated in FIG. 12. References identical to those already used previously designate identical or corresponding elements. In particular, there is again the flexible umbilical 200, which groups together the hydraulic and electrical connections and the print head 1, to which the printer architecture described below may be connected.

In this FIG. 12, it may be seen that the fluidic circuit 400 of the printer comprises a plurality of means 410, 500, 110, 210, 310, each associated with a specific functionality.

With this circuit 400 are associated a removable ink cartridge 130 and a solvent cartridge 140, also removable.

The reference 410 designates the main reservoir, which makes it possible to collect a mixture of solvent and ink.

The reference 110 designates the set of means that make it possible to withdraw, and potentially to store, solvent from a solvent cartridge 140 and to supply the solvent thus withdrawn to other parts of the printer, whether it involves supplying the main reservoir 410 with solvent, or cleaning or maintaining one or more of the other parts of the machine.

The reference 310 designates the set of means that make it possible to withdraw ink from an ink cartridge 130 and to provide the ink thus withdrawn to supply the main reservoir 410. As may be seen in this figure, according to the embodiment described here, the sending, to the main reservoir 410 and from the means 110, of solvent, goes through these same means 310.

At the outlet of the reservoir 410, a set of means, globally designated by the reference 210, makes it possible to pressurise the ink withdrawn from the main reservoir, and to send it to the print head 1. According to one embodiment, illustrated here by the arrow 250, it is also possible, by these means 210, to send ink to the means 310, then once again to the reservoir 410, which enables a recirculation of the ink inside the circuit. This circuit 210 also makes it possible to empty the reservoir in the cartridge 130 and to clean the connections of the cartridge 130

The system represented in this figure also comprises means 500 for recovering fluids (ink and/or solvent) which return from the print head, more exactly the gutter 7 of the print head or the circuit for rinsing the head. These means 500 are thus arranged downstream of the umbilical 200 (with respect to the direction of circulation of the fluids that return from the print head).

As may be seen in FIG. 12, the means 11 may also make it possible to send solvent directly to these means 500, without going through either the umbilical 200 or through the print head 1 or through the recovery gutter.

The means 110 may comprise at least 3 parallel supplies of solvent, one to the head 1, the $2^{nd}$ to the means 500 and the $3^{rd}$ to the means 310.

Each of the means described above is provided with means, such as valves, preferably electromagnetic valves, which make it possible to orient the fluid concerned to the chosen destination. Thus, from the means 110, it is possible to send exclusively solvent to the head 1, or to the means 500 or to the means 310.

Each of the means 500, 110, 210, 310 described above is provided with a pump that makes it possible to treat the fluid concerned (respectively: $1^{st}$ pump, $2^{nd}$ pump, $3^{rd}$ pump, $4^{th}$ pump). These different pumps ensure different functions (those of their respective means) and are thus different to each other, even if these different pumps may be of same or similar type: none of these pumps ensures 2 of these functions).

In particular, the means 500 comprise a pump ($1^{st}$ pump) which makes it possible to pump the fluid, recovered, as explained above, from the print head, and to send it to the main reservoir 410. This pump is dedicated to the recovery of this fluid coming from the print head and is physically different to the $4^{th}$ pump of the means 310 dedicated to the transfer of ink or the $3^{rd}$ pump of the means 210 dedicated to the pressurisation of ink at the outlet of the reservoir 410.

The means 110 comprise a pump (the $2^{nd}$ pump) which makes it possible to pump solvent and to send it to the means 500 and/or to the means 310 and/or to the print head 1. It is for example the pump 72 of FIG. 11.

A device for measuring flow rate, and potentially viscosity, according to the invention is situated in the print head or upstream, for example as explained above in relation with FIG. 3B. The print head is for example that described above in relation with FIG. 8. The assembly comprising the device for measuring flow rate (and potentially viscosity) and the print head has for example the structure described above in relation with FIG. 9A or 9B. Control or servo-control means have been described above, in particular in relation with FIG. 11.

Figure 13A:
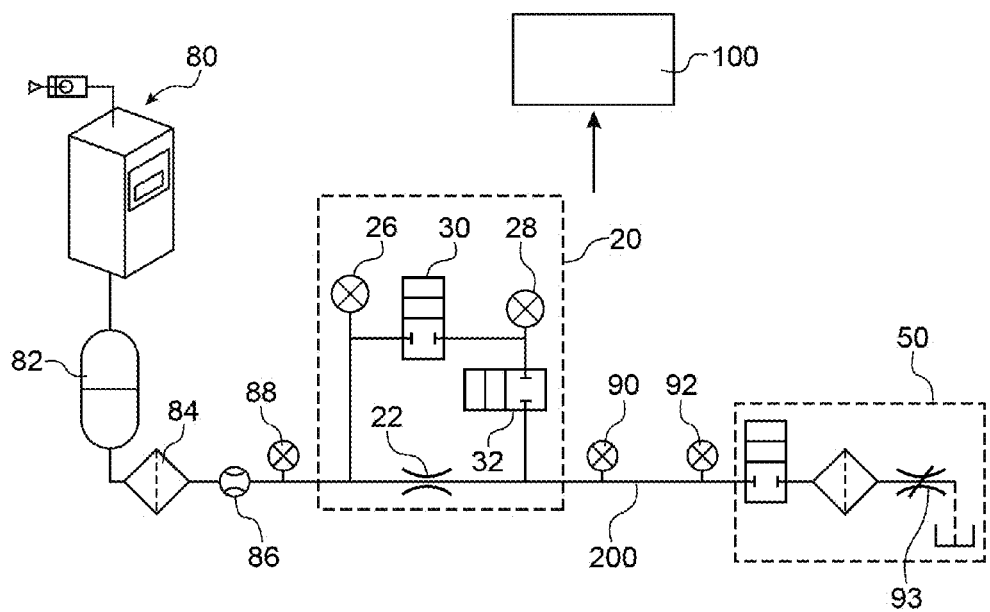
FIGS. 13A, 13B and 13C represent examples of device for measuring hydraulic coefficients in a device according to the invention.
Figure 13B:
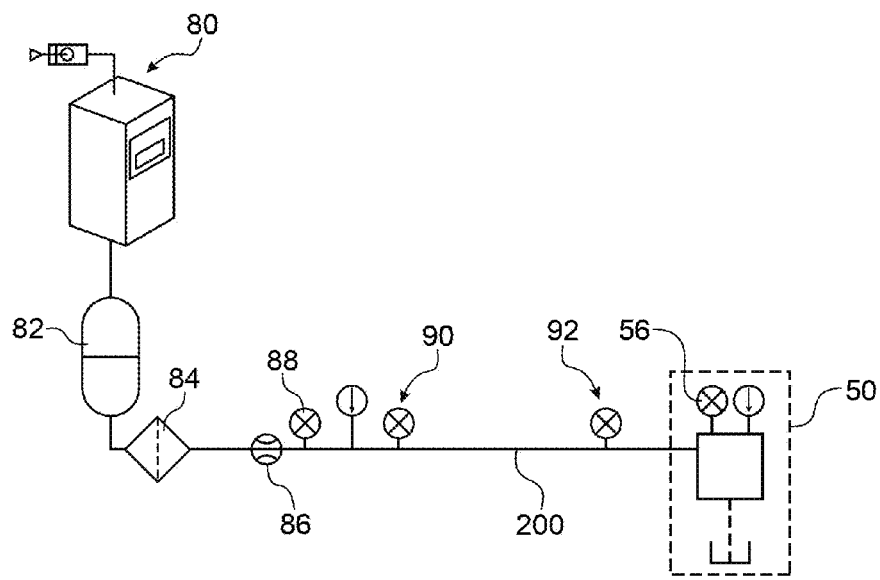

To determine the coefficients $\beta_0$ or $\alpha$Head, $\beta$Head, for example at the moment of production of the printers, it is possible to use a mounting such as that illustrated in FIG. 13A or 13B, which comprises an assembly for generating a precisely regulated pressurised fluid. This assembly comprises a reserve 82 of fluid pressurised by compressed air using a pressure regulator 80, preferably electrically commanded, to impose a regulated pressure in the circuit, for example at least 4 bars from a pressure source of at least 7 bars. The electrically commanded pressure regulator 80 makes it possible, from a voltage value, to obtain a pressure that is maintained constant in the reservoir 82. This assembly supplies a filter 84, a precision flow rate sensor 86, a pressure sensor 88, the element to test, and of which it is wished to determine the parameters $\alpha$ and $\beta$ (on FIG. 12A it is the flow meter 20 described above). The calibrated orifice 93 simulates the operation of the head when identifying the parameters $\alpha$ and $\beta$ of the flow meter. The sensor 88 is a reference pressure sensor. It makes it possible to verify, by coherence, that the other sensors equipping the flow meter and/or the print head do not supply aberrant values.

In the case of a measurement of the parameters $\alpha$Head and $\beta$Head of a print head 50 (FIG. 13B), this replaces the calibrated orifice 93, as illustrated in FIG. 13B. This configuration allows a measurement of the parameters of the head 50 for a device like the one of FIG. 9B.

In a variant, the system of FIG. 13A could characterise both the 2 components (flow meter 200 and head 50) by maintaining the flow meter 20 in place and by replacing the orifice 93 by the print head 50.

Figure 13C:
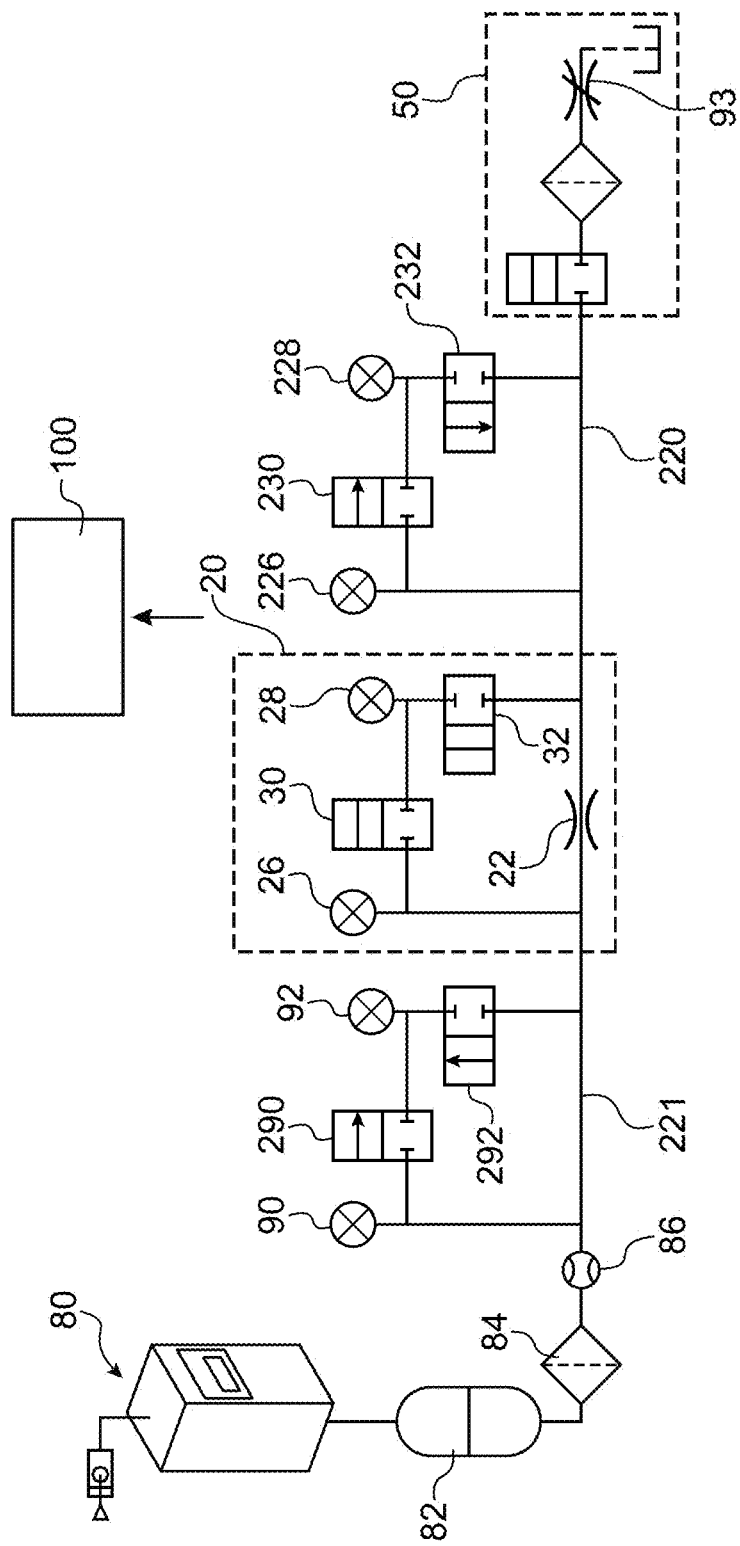

To determine the coefficients $\alpha$F, $\beta$F, $\beta$v in the case of the device of FIGS. 10A-10D, for example at the moment of production of the printers, it is possible to use a mounting such as that illustrated in FIG. 13C, which comprises an assembly for generating a precisely regulated pressurised fluid.

References identical to those of the preceding references designate the same elements, with the same technical advantages.

Upstream of the flow meter 20 (of which it is wished to determine the hydraulic characteristics, similarly for the viscometer 220, 226-232) is positioned a conduit or pipe 221 of which the hydraulic characteristics are known. The references 290 and 292 represent valves.

In the 4 cases, the use of a Coriolis type flow meter 86 has the advantage of enabling a very precise measurement of the flow rate, the temperature and the specific gravity (or volumetric mass density ($\rho$) (also called density, in kg/m3 for example) of the fluid.

The viscosity measurement may be carried out simply by withdrawal of fluid then measurement in the laboratory on a Couette type viscometer (of which the precision is satisfactory). In a variant, it is possible to measure the viscosity using 2 pressure sensors 90 and 92 arranged as indicated in FIGS. 13A and 13B, at the ends of an umbilical 200 (Pin$\mu$–Pout$\mu$). On FIG. 13C there is no umbilical 200, but the measurement of the pressure difference between the 2 sensors 90 and 92 provides information on the viscosity. The pressure difference between the 2 sensors 90 and 92 provides direct information on the viscosity of the fluid (a first calibration makes it possible to determine the relation between head loss and viscosity (calibration of the viscometer) then the viscosity is obtained from the pressure difference between 90 and 92). Advantageously, a calibration (correspondence curve) between the measurement (Pin$\mu$–Pout$\mu$) and the measurement of viscosity in the laboratory makes it possible to obtain the viscosity measurement directly, without other in-line measurements (thus without measurement of the pressure, the specific gravity (or density, for example in kg/m³), the temperature, or the flow rate).

Such a device makes it possible to collect data that is going to make it possible to link, on the one hand, the pressure difference, (Pin−Pout)/q (or (PinF−PoutF)/q and (PinV−PoutV)/q) and, on the other hand, the flow rate q, and finally to obtain the coefficients (α, β) or (αF, βF) and βv. A data acquisition system 100 makes it possible to collect all of the items of information necessary for the calculations of the hydraulic coefficients for example (α, β) or (αHead, βHead) or (αF, βF) and βv.

This system 100 comprises for example a micro-computer or a micro-processor and/or an electronic or electric circuit, preferably programmable, which is going to collect the items of information of flow rate or pressure or pressure differences supplied by the sensors 86, 88, and possibly 90, 92, the potential items of information of temperature, and calculate or estimate (Pin−Pout), q, and the coefficients (α, β). Advantageously, this system 100 also manages the pressure regulator 20, the reserve 82; the result is thus an automated system for characterising components (flow meter and/or head).

During printing on a support 800, a flow rate and/or viscosity measurement may be carried out using a device according to the invention; a correction of the flow rate and/or the viscosity may be implemented during printing.

The flow rate of ink sent to the print head is for example at least equal to 60 ml/h (this may notably be the case for a single jet head equipped with a small nozzle) and may reach 6000 ml/h (this may notably be the case for a multi-jet head (for example with 128 jets)); it may be well above 6000 ml/h for multi-jet head assemblies.

The invention claimed is:

1. Device for measuring the flow rate of ink sent to a print head of an ink jet printer, comprising:
   a restriction of the diameter of a conduit for the flow of ink, arranged in the path thereof defined by said conduit,
   at least one sensor for measuring the pressure difference $(P_{in}-P_{out})$, between the pressure of fluid upstream of the restriction $(P_{in})$ and the pressure of ink downstream of the restriction $(P_{out})$,
   a circuit or a controller for calculating the flow rate of ink as a function of the pressure difference $(P_{in}-P_{out})$, and
   a pressure sensor situated in the print head for measuring pressure in the print head.

2. Device according to claim 1, said circuit or controller being capable of, or programmed to, calculate it as a function of the hydraulic characteristics (α, β) of the restriction, the specific gravity (ρ) and the viscosity (μ) of the ink, and said pressure difference $(P_{in}-P_{out})$.

3. Device according to claim 1, said at least one sensor comprising:
   a sensor for measuring the differential pressure between the pressure of fluid upstream of the restriction and the pressure of fluid downstream of the restriction, without measurement of each of these 2 pressures separately;
   or a single sensor for measuring pressure and at least a valve for placing the latter in fluidic communication alternatively with fluid upstream of the restriction and fluid downstream of the restriction;
   or a $1^{st}$ sensor for measuring the pressure of ink upstream of the restriction and a $2^{nd}$ sensor for measuring the pressure of ink downstream of the restriction.

4. Device according to claim 1, said at least one sensor comprising a $1^{st}$ sensor for measuring the pressure of ink upstream of the restriction and a $2^{nd}$ sensor for measuring the pressure of ink downstream of the restriction, and the device further comprising at least a valve for opening or closing a fluidic communication between the $1^{st}$ sensor and the $2^{nd}$ sensor, and at least a valve for opening or closing a fluidic communication between the $2^{nd}$ sensor and a point of a conduit downstream of the restriction.

5. Device according to claim 1 comprising a $1^{st}$ sensor for measuring the pressure of ink upstream of the restriction and a $2^{nd}$ sensor for measuring the pressure of ink downstream of the restriction, said circuit or controller being capable of, or programmed for, correcting a measurement difference, for at least one same pressure, between the $1^{st}$ sensor and the $2^{nd}$ sensor and/or a sensitivity error of at least one of the sensors.

6. Device according to claim 5, further comprising a temperature sensor, the measurement difference, for at least one same pressure and/or the sensitivity error of at least one of the sensors being corrected as a function of temperature.

7. Device according to claim 1, said at least one sensor being arranged in the path of a fluidic conduit arranged in parallel with the restriction.

8. Device for measuring the flow rate and the viscosity of ink of an ink jet printer comprising a device for measuring the flow rate of ink supplied to a print head of the printer, according to claim 1, and at least one sensor for measuring viscosity.

9. Device according to claim 8, further comprising a circuit or a controller for calculating the viscosity of ink as a function of the pressure (PHead) measured in the print head by said pressure sensor.

10. Device according to claim 9, said circuit or controller for calculating the viscosity of ink being capable of, or programmed to, calculate it as a function of the hydraulic characteristics (αHead, βHead) of the print head, and the pressure measured by the pressure sensor of the head.

11. Device according to claim 8, comprising a circuit or controller capable of, or programmed for, correcting a measurement difference, for at least one pressure, between a pressure value measured by the pressure sensor of the head and said actual or real pressure.

12. Device according to claim 11, further comprising a temperature sensor, the measurement difference, for at least one pressure, between a pressure value measured by the pressure sensor of the head and said actual pressure, being corrected as a function of temperature.

13. Device according to claim 8, comprising a conduit, arranged in series with said device for measuring the flow rate of ink, and at least a sensor for measuring a pressure difference (Poutv−Pinv) between an inlet and an outlet of said conduit.

14. Device according to claim 13, comprising a same common sensor making it possible to measure:
   the pressure of ink downstream of the restriction and the pressure at the inlet of said conduit arranged in series with said device for measuring the flow rate of ink;
   or the pressure of ink downstream of the restriction, and the pressures at the inlet and at the outlet of said conduit arranged in series with said device for measuring the flow rate of ink, said device comprising for example at least a valve for opening or closing a fluidic communication between said common sensor and a point downstream of said conduit;
   or the pressure of ink upstream of the restriction and the pressure at the outlet of said conduit arranged in series with said device for measuring the flow rate of ink.

15. Circuit for supplying with ink and/or with solvent an ink jet printer, this circuit comprising a device for measuring the flow rate, or the flow rate and the viscosity, of the ink of an ink jet printer, according to claim 1, and a circuit or a controller for controlling or servo-controlling or correcting the pressure and/or the viscosity of ink supplied as a function of the measurements of the flow rate, or the flow rate and the viscosity of the ink.

16. Fluidic connecting cable, for ink jet printer, this cable comprising a device for measuring flow rate, or flow rate and viscosity, according to claim 1.

17. Ink jet printer comprising:
a print head, with one jet or multi-jet;
a hydraulic circuit for forming a flow of fluid to send to said print head;
a fluidic connecting cable between said hydraulic circuit for forming a flow of fluid and the print head; and
a device for measuring the flow rate of said fluid according to claim 1.

18. Ink jet printer according to claim 17, further comprising a device for measuring the flow rate and the viscosity of said fluid, including the device for measuring the flow rate of ink supplied to a print head of the printer and at least one sensor for measuring viscosity.

19. Ink jet printer according to claim 17, the print head comprising a pressure sensor, and a circuit or a controller capable of, or programmed for, calculating the viscosity of the ink as a function of the pressure (PHead) measured by said pressure sensor, for example as a function of the hydraulic characteristics (αHead, βHead) of the print head, and of the pressure measured by said pressure sensor.

20. Printer according to claim 19, said circuit or controller being capable of, or programmed for:
correcting, preferably as a function of temperature, a measurement difference, for at least one pressure, between a pressure value measured by the pressure sensor of the head and said actual or real pressure;
and/or for controlling or servo-controlling or correcting the pressure and/or the viscosity of ink as a function of the measurements of the flow rate and/or the viscosity of the ink.

21. Device for measuring the flow rate of ink sent to a print head of an ink jet printer, comprising:
a restriction of the diameter of a conduit for the flow of ink, arranged in the path thereof defined by said conduit,
at least one sensor for measuring the pressure difference ($P_{in}$–$P_{out}$), between the pressure of fluid upstream of the restriction ($P_{in}$) and the pressure of ink downstream of the restriction ($P_{out}$),
means for calculating the flow rate of ink as a function of the pressure difference ($P_{in}$–$P_{out}$) and
a pressure sensor situated in the print head for measuring pressure in the print head.

* * * * *

UNITED STATES PATENT AND TRADEMARK OFFICE
CERTIFICATE OF CORRECTION

PATENT NO. : 10,065,427 B2
APPLICATION NO. : 15/465888
DATED : September 4, 2018
INVENTOR(S) : Alain Pagnon et al.

Page 1 of 1

It is certified that error appears in the above-identified patent and that said Letters Patent is hereby corrected as shown below:

In the Specification

Column 26, Line 26, "3.0" should be -- 3.1 --.

Signed and Sealed this
Thirteenth Day of November, 2018

Andrei Iancu
*Director of the United States Patent and Trademark Office*